US008722739B2

(12) United States Patent
deLong et al.

(10) Patent No.: US 8,722,739 B2

(45) Date of Patent: May 13, 2014

(54) AMINO ACID SALTS OF PROSTAGLANDINS

(75) Inventors: Mitchell A. deLong, Raleigh, NC (US); Jill Marie Sturdivant, Chapel Hill, NC (US)

(73) Assignee: Novaer Holdings, Inc., Bedminster, NJ (US)

(*) Notice: Subject to any disclaimer, the term of this patent is extended or adjusted under 35 U.S.C. 154(b) by 545 days.

(21) Appl. No.: 12/260,522

(22) Filed: Oct. 29, 2008

(65) Prior Publication Data

US 2010/0105771 A1 Apr. 29, 2010

(51) Int. Cl.

| | |
|---|---|
| ***A61K 31/195*** | (2006.01) |
| ***A61K 31/5575*** | (2006.01) |
| ***C07C 57/26*** | (2006.01) |
| ***C07C 229/26*** | (2006.01) |

(52) U.S. Cl.

CPC ............ *A61K 31/5575* (2013.01); *C07C 57/26* (2013.01); *C07C 229/26* (2013.01)

USPC ........... 514/567; 514/530; 514/559; 554/117; 554/222

(58) Field of Classification Search

CPC .. C07C 57/26; A61K 31/5575; A61K 31/195; A61K 8/67; C10M 2207/281; C10M 2207/283

See application file for complete search history.

(56) References Cited

U.S. PATENT DOCUMENTS

| | | | | |
|---|---|---|---|---|
| 13,294 | A | 7/1855 | Reynolds | |
| 37,913 | A | 3/1863 | Howe | |
| 37,914 | A | 3/1863 | Hankinson | |
| 146,439 | A | 1/1874 | Ellis | |
| 3,382,247 | A | 5/1968 | Anthony | |
| 3,435,053 | A | 3/1969 | Beal et al. | |
| 3,524,867 | A | 8/1970 | Beal et al. | |
| 3,598,858 | A | 8/1971 | Bergstrom et al. | |
| 3,636,120 | A | 1/1972 | Pike | |
| 3,644,363 | A | 2/1972 | Kim | |
| 3,691,216 | A | 9/1972 | Bergstrom et al. | |
| 3,706,789 | A | 12/1972 | Bergstrom et al. | |
| 3,723,427 | A | 3/1973 | Susi | |
| 3,776,938 | A | 12/1973 | Bergstrom et al. | |
| 3,776,939 | A | 12/1973 | Bergstrom et al. | |
| 3,798,275 | A | 3/1974 | Finch et al. | |
| 3,839,409 | A | 10/1974 | Bergstrom et al. | |
| 3,852,337 | A | 12/1974 | Bergstrom et al. | |
| 3,882,241 | A | 5/1975 | Phariss | |
| 3,882,245 | A | 5/1975 | DuChame | |
| 3,896,156 | A | 7/1975 | Beal et al. | |
| 3,928,588 | A | 12/1975 | Robert | |
| 3,931,282 | A * | 1/1976 | Muchowski et al. | 560/121 |
| 3,934,013 | A | 1/1976 | Poulsen | |
| 3,966,792 | A | 6/1976 | Hayashi et al. | |
| 3,974,213 | A | 8/1976 | Hess et al. | |
| 3,984,424 | A | 10/1976 | Schaff | |
| 3,984,455 | A * | 10/1976 | Beal et al. | 560/121 |
| 3,985,791 | A | 10/1976 | Muchowski et al. | |
| 4,004,020 | A | 1/1977 | Skuballa et al. | |
| 4,005,133 | A * | 1/1977 | Morozowich | 562/503 |
| 4,011,262 | A | 3/1977 | Hess et al. | |
| 4,018,812 | A | 4/1977 | Hayashi et al. | |
| 4,024,179 | A | 5/1977 | Bindra et al. | |
| 4,051,238 | A | 9/1977 | Sokolowski | |
| 4,061,671 | A | 12/1977 | Beck et al. | |
| 4,073,934 | A | 2/1978 | Skuballa et al. | |
| 4,089,885 | A | 5/1978 | Husbands | |
| 4,105,854 | A | 8/1978 | Gibson | |
| 4,116,989 | A | 9/1978 | Nelson | |
| 4,123,441 | A | 10/1978 | Johnson | |
| 4,128,577 | A | 12/1978 | Nelson | |
| 4,128,720 | A | 12/1978 | Hayashi et al. | |
| 4,139,619 | A | 2/1979 | Chidsey, III | |
| 4,152,527 | A | 5/1979 | Hess et al. | |
| 4,154,950 | A | 5/1979 | Nelson | |
| 4,158,667 | A | 6/1979 | Axen | |
| 4,171,331 | A | 10/1979 | Biddlecom et al. | |
| 4,206,151 | A | 6/1980 | Grudzinskas | |
| 4,217,360 | A | 8/1980 | Vorbruggen et al. | |
| 4,225,507 | A | 9/1980 | Sih | |
| 4,225,508 | A | 9/1980 | Sih | |
| 4,268,522 | A | 5/1981 | Eggler et al. | |
| 4,284,646 | A | 8/1981 | Vorbruggen et al. | |
| 4,296,504 | A | 10/1981 | Lawson | |
| 4,311,707 | A | 1/1982 | Birnbaum et al. | |
| 4,489,092 | A | 12/1984 | Vorbruggen et al. | |
| 4,499,293 | A | 2/1985 | Johnson et al. | |
| 4,543,353 | A | 9/1985 | Faustini et al. | |
| 4,596,812 | A | 6/1986 | Chidsey | |
| 4,599,353 | A | 7/1986 | Bito | |
| 4,621,100 | A | 11/1986 | Lund et al. | |

(Continued)

FOREIGN PATENT DOCUMENTS

| | | |
|---|---|---|
| BE | 746615 | 7/1970 |
| CA | 1339132 | 7/1997 |

(Continued)

OTHER PUBLICATIONS

Adeyeye, Moju, ed., Preformulatin in solid Dosage form Development, 2008, Informa Healthcare, Chapter 2.3, pp. 63-80.*

Bastin et al., Salt Selection and Optimisation Procedures for Pharmaceutical new Chemical Entities, 2000, Organic Process Research & Development, vo. 4, No. 5, pp. 427-435.*

Berge et al., Pharmaceutical Salts, 1997, Journal of Pharmaceutical Scienes, vo. 66, No. 1, pp. 1-19.*

Liu, Rong, ed., Water-Insoluble Drug Formulation , 2008, CRC press, Chapter 15, pp. 417-435.*

Stahl et al. eds., Handbood of Pharmaceutical Salts, Propeties, Selection and Use, 2008, Wiley-Vch, Chapter 12, 265-327 (33 pages).*

Swarbrick et al, eds., Encyclopedia of Pharmaceutical Technology, 1988, Marcel Dekker, Inc. vol. 13, pp. 453-499 (48 pages).*

Wand, M., "Latanoprost and hyperpigmentation of eyelashes," Archives of Ophthalmology (1997) 115(9):1206-1208.

(Continued)

*Primary Examiner* — Yate K Cutliff

(74) *Attorney, Agent, or Firm* — Greenberg Traurig, LLP

(57) ABSTRACT

The present invention is directed to novel amino acid prostaglandin salts and methods of making and using them.

8 Claims, No Drawings

(56) References Cited

U.S. PATENT DOCUMENTS

| | | | | |
|---|---|---|---|---|
| 4,704,386 | A | 11/1987 | Mueller | |
| 4,757,089 | A | 7/1988 | Epstein | |
| 4,812,457 | A | 3/1989 | Narumiya et al. | |
| 4,883,819 | A | 11/1989 | Bito | |
| 4,889,845 | A | 12/1989 | Ritter et al. | |
| 4,912,235 | A * | 3/1990 | Cooper et al. | 549/427 |
| 4,952,581 | A | 8/1990 | Bito et al. | |
| 4,968,812 | A | 11/1990 | Wang et al. | |
| 5,001,153 | A | 3/1991 | Ueno | |
| 5,041,439 | A | 8/1991 | Kasting et al. | |
| 5,063,057 | A | 11/1991 | Spellman et al. | |
| 5,166,178 | A | 11/1992 | Ueno et al. | |
| 5,194,429 | A | 3/1993 | Ueno | |
| 5,212,324 | A | 5/1993 | Ueno et al. | |
| 5,219,885 | A | 6/1993 | Frolich et al. | |
| 5,280,018 | A | 1/1994 | Ritter et al. | |
| 5,288,754 | A | 2/1994 | Woodward et al. | |
| 5,296,504 | A | 3/1994 | Stjernschantz et al. | |
| 5,302,617 | A | 4/1994 | Ueno | |
| 5,312,832 | A | 5/1994 | Chan | |
| 5,321,128 | A | 6/1994 | Stjernschantz et al. | |
| 5,332,730 | A | 7/1994 | Chan | |
| 5,340,813 | A | 8/1994 | Klein et al. | |
| 5,352,708 | A | 10/1994 | Woodward et al. | |
| 5,409,911 | A | 4/1995 | Tyler et al. | |
| 5,422,368 | A | 6/1995 | Stjernschantz | |
| 5,422,369 | A | 6/1995 | Stjernschantz | |
| 5,422,371 | A | 6/1995 | Liao et al. | |
| 5,426,115 | A | 6/1995 | Ueno et al. | |
| 5,431,881 | A | 7/1995 | Palacios | |
| 5,458,883 | A | 10/1995 | Epstein | |
| 5,464,868 | A | 11/1995 | Frolich et al. | |
| 5,480,900 | A | 1/1996 | DeSantis, Jr. et al. | |
| 5,500,230 | A | 3/1996 | Nathanson | |
| 5,508,303 | A | 4/1996 | Isogaya et al. | |
| 5,510,383 | A | 4/1996 | Bishop | |
| 5,516,652 | A | 5/1996 | Abramovitz et al. | |
| 5,567,079 | A | 10/1996 | Felder | |
| 5,576,315 | A | 11/1996 | Hallinan et al. | |
| 5,578,618 | A | 11/1996 | Stjernschantz et al. | |
| 5,578,640 | A | 11/1996 | Hanson | |
| 5,578,643 | A | 11/1996 | Hanson | |
| 5,587,391 | A | 12/1996 | Burk | |
| 5,605,814 | A | 2/1997 | Abramovitz et al. | |
| 5,605,931 | A | 2/1997 | Hanson | |
| 5,607,978 | A | 3/1997 | Woodward et al. | |
| 5,627,208 | A | 5/1997 | Stjernschantz et al. | |
| 5,641,494 | A | 6/1997 | Cauwenbergh | |
| 5,658,897 | A | 8/1997 | Burk | |
| 5,663,203 | A | 9/1997 | Ekerdt et al. | |
| 5,665,773 | A | 9/1997 | Klimko et al. | |
| 5,670,506 | A | 9/1997 | Leigh et al. | |
| 5,681,850 | A | 10/1997 | Frolich et al. | |
| 5,688,819 | A | 11/1997 | Woodward et al. | |
| 5,698,733 | A | 12/1997 | Hellberg et al. | |
| 5,703,108 | A | 12/1997 | Cameron et al. | |
| 5,716,609 | A | 2/1998 | Jain et al. | |
| 5,719,140 | A | 2/1998 | Chandrakumar et al. | |
| 5,741,810 | A | 4/1998 | Burk | |
| 5,759,789 | A | 6/1998 | Abramovitz et al. | |
| 5,770,759 | A | 6/1998 | Ueno et al. | |
| 5,773,472 | A | 6/1998 | Stjernschantz | |
| 5,792,851 | A | 8/1998 | Schuster et al. | |
| 5,834,498 | A | 11/1998 | Burk | |
| 5,840,847 | A | 11/1998 | Abramovitz et al. | |
| 5,849,791 | A | 12/1998 | Stjernschantz et al. | |
| 5,863,948 | A | 1/1999 | Epstein et al. | |
| 5,869,281 | A | 2/1999 | Abramovitz et al. | |
| 5,877,211 | A | 3/1999 | Woodward | |
| 5,885,766 | A | 3/1999 | Mahe et al. | |
| 5,885,974 | A | 3/1999 | Danielov | |
| 5,889,052 | A | 3/1999 | Klimko et al. | |
| 5,892,099 | A | 4/1999 | Maruyama et al. | |
| 5,958,723 | A | 9/1999 | Abramovitz et al. | |
| 5,972,965 | A | 10/1999 | Taniguchi et al. | |
| 5,973,002 | A | 10/1999 | Frolich et al. | |
| 5,977,173 | A | 11/1999 | Wos et al. | |
| 5,985,597 | A | 11/1999 | Ford-Hutchinson et al. | |
| 5,990,346 | A | 11/1999 | Kataoka et al. | |
| 5,994,397 | A | 11/1999 | Selliah et al. | |
| 6,013,823 | A | 1/2000 | Mamarella et al. | |
| 6,025,375 | A | 2/2000 | Taniguchi et al. | |
| 6,025,392 | A | 2/2000 | Selliah et al. | |
| 6,030,959 | A | 2/2000 | Tremont et al. | |
| 6,030,999 | A | 2/2000 | Stjemschantz et al. | |
| 6,031,001 | A | 2/2000 | Stjemschantz et al. | |
| 6,031,079 | A | 2/2000 | Ford-Hutchinson et al. | |
| 6,037,364 | A | 3/2000 | Burk | |
| 6,037,368 | A | 3/2000 | Podos et al. | |
| 6,043,264 | A | 3/2000 | Ohtake et al. | |
| 6,048,895 | A | 4/2000 | Wos et al. | |
| 6,107,338 | A | 8/2000 | Wos et al. | |
| 6,110,969 | A | 8/2000 | Tani et al. | |
| 6,121,253 | A | 9/2000 | Han et al. | |
| 6,124,344 | A | 9/2000 | Burk | |
| 6,126,957 | A | 10/2000 | Epstein | |
| 6,160,129 | A | 12/2000 | Burk | |
| 6,169,111 | B1 | 1/2001 | Zinke et al. | |
| 6,232,344 | B1 | 5/2001 | Feng et al. | |
| 6,262,105 | B1 | 7/2001 | Johnstone | |
| 6,372,730 | B1 | 4/2002 | deLong et al. | |
| 6,403,649 | B1 | 6/2002 | Woodward et al. | |
| 6,410,780 | B1 | 6/2002 | deLong et al. | |
| 6,441,047 | B2 | 8/2002 | De Santis, Jr. | |
| 6,444,840 | B1 | 9/2002 | deLong et al. | |
| 6,451,859 | B1 | 9/2002 | deLong et al. | |
| 6,534,082 | B1 | 3/2003 | Epstein | |
| 6,548,535 | B2 | 4/2003 | Garcia et al. | |
| 6,586,463 | B2 | 7/2003 | deLong et al. | |
| 6,716,876 | B2 | 4/2004 | Burk | |
| 6,894,175 | B1 | 5/2005 | deLong | |
| 7,045,634 | B2 | 5/2006 | Krauss et al. | |
| 7,070,768 | B2 | 7/2006 | Krauss | |
| 7,074,942 | B2 | 7/2006 | deLong | |
| 7,115,659 | B2 | 10/2006 | deLong | |
| 7,157,590 | B2 * | 1/2007 | Gutman et al. | 554/142 |
| 7,288,029 | B1 | 10/2007 | Lyon | |
| 7,320,967 | B2 | 1/2008 | Michelet et al. | |
| 7,388,029 | B2 | 6/2008 | deLong et al. | |
| 7,407,987 | B2 | 8/2008 | deLong et al. | |
| 7,521,530 | B2 | 4/2009 | Peri et al. | |
| 7,589,233 | B2 * | 9/2009 | Chandran | 562/570 |
| 2001/0047025 | A1 | 11/2001 | Garcia et al. | |
| 2002/0013294 | A1 | 1/2002 | deLong et al. | |
| 2002/0037914 | A1 | 3/2002 | deLong et al. | |
| 2002/0044953 | A1 | 4/2002 | Michelet et al. | |
| 2002/0045659 | A1 | 4/2002 | Michelet et al. | |
| 2002/0052414 | A1 | 5/2002 | Bernard et al. | |
| 2002/0146439 | A1 | 10/2002 | deLong et al. | |
| 2002/0172693 | A1 | 11/2002 | deLong et al. | |
| 2003/0083381 | A1 | 5/2003 | Kumagai et al. | |
| 2003/0147823 | A1 | 8/2003 | Woodward et al. | |
| 2003/0165549 | A1 | 9/2003 | Bernard et al. | |
| 2003/0191173 | A1 | 10/2003 | Garcia et al. | |
| 2003/0199590 | A1 | 10/2003 | Cagle | |
| 2004/0082013 | A1 | 4/2004 | Regan | |
| 2004/0157912 | A1 | 8/2004 | Old et al. | |
| 2004/0167190 | A1 | 8/2004 | Stjernschantz et al. | |
| 2004/0171596 | A1 | 9/2004 | Prokai et al. | |
| 2005/0058614 | A1 | 3/2005 | Krauss | |
| 2005/0112075 | A1 | 5/2005 | Hwang et al. | |
| 2006/0106078 | A1 | 5/2006 | Krauss et al. | |
| 2006/0121069 | A1 | 6/2006 | deLong et al. | |
| 2006/0135609 | A1 | 6/2006 | Toone et al. | |
| 2006/0247214 | A1 | 11/2006 | deLong et al. | |
| 2007/0004620 | A1 | 1/2007 | Jabbour et al. | |
| 2007/0161699 | A1 | 7/2007 | Epstein et al. | |
| 2007/0254920 | A1 | 11/2007 | deLong et al. | |
| 2007/0282006 | A1 | 12/2007 | Woodward et al. | |
| 2008/0070988 | A1 | 3/2008 | Woodward et al. | |
| 2008/0096240 | A1 | 4/2008 | Woodward et al. | |
| 2008/0103184 | A1 | 5/2008 | deLong et al. | |
| 2008/0241078 | A1 | 10/2008 | deLong et al. | |
| 2009/0018204 | A1 | 1/2009 | Brinkenhoff | |

(56) References Cited

U.S. PATENT DOCUMENTS

| | | | |
|---|---|---|---|
| 2009/0203659 | A1 | 8/2009 | Woodward et al. |
| 2009/0286769 | A1 | 11/2009 | deLong et al. |
| 2010/0105775 | A1 | 4/2010 | deLong et al. |

FOREIGN PATENT DOCUMENTS

| | | |
|---|---|---|
| DE | 1801750 | 7/1969 |
| DE | 1617477 | 1/1970 |
| DE | 2255731 | 5/1973 |
| DE | 2355731 | 5/1974 |
| DE | 2409460 | 8/1974 |
| DE | 2460990 | 12/1974 |
| DE | 2365101 | 7/1975 |
| DE | 24 60 990 | 7/1976 |
| DE | 2605584 | 8/1976 |
| DE | 2605242 | 9/1976 |
| DE | 2517771 | 10/1976 |
| DE | 2737808 | 3/1978 |
| EP | 0170258 | 2/1986 |
| EP | 249194 | 6/1986 |
| EP | 0295092 | 12/1988 |
| EP | 0308135 | 3/1989 |
| EP | 0342003 | 5/1989 |
| EP | 572014 | 1/1993 |
| EP | 639563 | 2/1995 |
| EP | 648488 | 4/1995 |
| EP | 1008588 | 2/1998 |
| EP | 857718 | 8/1998 |
| EP | 1016660 | 9/1998 |
| EP | 911321 | 4/1999 |
| EP | 925787 | 6/1999 |
| EP | 970697 | 9/1999 |
| EP | 947500 | 10/1999 |
| FR | 2108027 | 9/1971 |
| FR | 2182928 | 12/1973 |
| FR | 2239458 | 2/1975 |
| FR | 2314712 | 1/1977 |
| FR | 2730811 | 2/1995 |
| GB | 1236227 | 6/1971 |
| GB | 1251750 | 10/1971 |
| GB | 1324737 | 10/1971 |
| GB | 1285371 | 8/1972 |
| GB | 1285372 | 8/1972 |
| GB | 1409841 | 5/1973 |
| GB | 1456512 | 11/1976 |
| GB | 1456513 | 11/1976 |
| GB | 1456514 | 11/1976 |
| GB | 1456838 | 11/1976 |
| GB | 1542569 | 3/1979 |
| GB | 1545411 | 5/1979 |
| GB | 2025413 | 7/1979 |
| GB | 2025413 | 1/1980 |
| GB | 2048254 | 12/1980 |
| GB | 2330307 | 4/1999 |
| JP | 49-47352 | 5/1973 |
| JP | 49-069636 | 7/1974 |
| JP | 49-093342 | 9/1974 |
| JP | 49-101356 | 9/1974 |
| JP | 49-102647 | 9/1974 |
| JP | 51-086449 | 7/1976 |
| JP | 52-012919 | 1/1977 |
| JP | 52-053841 | 4/1977 |
| JP | 53-028160 | 3/1978 |
| JP | 58-029710 | 2/1983 |
| JP | 60-032763 | 2/1985 |
| JP | 61-218510 | 9/1986 |
| JP | 63-211231 | 9/1988 |
| JP | 02-85248 | 5/1989 |
| JP | 02 022226 | 1/1990 |
| JP | 03034934 | 2/1991 |
| JP | 3-83925 | 4/1991 |
| JP | 3-83926 | 4/1991 |
| JP | 4-300833 | 10/1992 |
| JP | 5-331025 | 12/1993 |
| JP | 9-295921 | 11/1997 |
| JP | 10-251225 | 9/1998 |
| JP | 10-287532 | 10/1998 |
| JP | 2003180399 | 7/2003 |
| WO | WO 86/00616 | 1/1986 |
| WO | WO 89/03384 | 4/1989 |
| WO | WO 90/02553 | 3/1990 |
| WO | WO 92/02495 | 2/1992 |
| WO | WO 94/08585 | 4/1994 |
| WO | WO 95/00552 | 1/1995 |
| WO | WO 95/11003 | 4/1995 |
| WO | WO 95/11033 | 4/1995 |
| WO | WO 95/18102 | 7/1995 |
| WO | WO 95/19165 | 7/1995 |
| WO | WO 95/19964 | 7/1995 |
| WO | WO 96/10407 | 4/1996 |
| WO | WO 96/36599 | 11/1996 |
| WO | WO 97/03973 | 2/1997 |
| WO | WO 97/09049 | 3/1997 |
| WO | WO 97/15319 | 5/1997 |
| WO | WO 97/23223 | 7/1997 |
| WO | WO 97/23225 | 7/1997 |
| WO | WO 97/23226 | 7/1997 |
| WO | WO 97/29735 | 8/1997 |
| WO | WO 97/31895 | 9/1997 |
| WO | WO 97/39754 | 10/1997 |
| WO | WO 98/00100 | 1/1998 |
| WO | WO 98/12175 | 3/1998 |
| WO | WO 98/13016 | 4/1998 |
| WO | WO 98/19680 | 5/1998 |
| WO | WO 98/20880 | 5/1998 |
| WO | WO 98/20881 | 5/1998 |
| WO | WO 98/21180 | 5/1998 |
| WO | WO 98/21181 | 5/1998 |
| WO | WO 98/21182 | 5/1998 |
| WO | WO 98/27976 | 7/1998 |
| WO | WO 98/28264 | 7/1998 |
| WO | WO 98/33497 | 8/1998 |
| WO | WO 98/39293 | 9/1998 |
| WO | 98/47515 | 10/1998 |
| WO | WO 98/50024 | 11/1998 |
| WO | WO 98/53809 | 12/1998 |
| WO | WO 98/57930 | 12/1998 |
| WO | WO 98/57942 | 12/1998 |
| WO | WO 98/58911 | 12/1998 |
| WO | WO 99/02165 | 1/1999 |
| WO | WO 99/12550 | 3/1999 |
| WO | WO 99/12551 | 3/1999 |
| WO | WO 99/12552 | 3/1999 |
| WO | WO 99/12553 | 3/1999 |
| WO | WO 99/12554 | 3/1999 |
| WO | WO 99/12555 | 3/1999 |
| WO | WO 99/12556 | 3/1999 |
| WO | WO 99/12557 | 3/1999 |
| WO | WO 99/12558 | 3/1999 |
| WO | WO 99/12559 | 3/1999 |
| WO | WO 99/12560 | 3/1999 |
| WO | WO 99/12561 | 3/1999 |
| WO | WO 99/12563 | 3/1999 |
| WO | WO 99/12895 | 3/1999 |
| WO | WO 99/12896 | 3/1999 |
| WO | WO 99/12897 | 3/1999 |
| WO | WO 99/12898 | 3/1999 |
| WO | WO 99/12899 | 3/1999 |
| WO | WO 99/19300 | 4/1999 |
| WO | WO 99/21562 | 5/1999 |
| WO | WO 99/22731 | 5/1999 |
| WO | WO 99/25357 | 5/1999 |
| WO | WO 99/25358 | 5/1999 |
| WO | WO 99/30675 | 6/1999 |
| WO | WO 99/30718 | 6/1999 |
| WO | WO 99/32441 | 7/1999 |
| WO | WO 99/32640 | 7/1999 |
| WO | WO 99/32641 | 7/1999 |
| WO | WO 99/33794 | 7/1999 |
| WO | WO 99/47497 | 9/1999 |
| WO | WO 99/50241 | 10/1999 |
| WO | WO 99/50242 | 10/1999 |
| WO | WO 99/61029 | 12/1999 |

(56) References Cited

FOREIGN PATENT DOCUMENTS

| | | |
|---|---|---|
| WO | WO 99/64621 | 12/1999 |
| WO | WO 99/65303 | 12/1999 |
| WO | WO 99/65527 | 12/1999 |
| WO | WO 00/02450 | 1/2000 |
| WO | WO 00/03736 | 1/2000 |
| WO | WO 00/03980 | 1/2000 |
| WO | WO 00/04898 | 2/2000 |
| WO | WO 00/04899 | 2/2000 |
| WO | WO 00/07627 | 2/2000 |
| WO | WO 00/09557 | 2/2000 |
| WO | WO 00/13664 | 3/2000 |
| WO | WO 00/15608 | 3/2000 |
| WO | WO 00/16760 | 3/2000 |
| WO | WO 00/51979 | 3/2000 |
| WO | WO 00/51971 | 9/2000 |
| WO | WO 00/51980 | 9/2000 |
| WO | WO 00/54810 | 9/2000 |
| WO | WO 01/10873 | 2/2001 |
| WO | WO 01/74307 | 10/2001 |
| WO | WO 01/74313 | 10/2001 |
| WO | WO 01/74314 | 10/2001 |
| WO | WO 01/74315 | 10/2001 |
| WO | 02/067901 | 9/2002 |
| WO | 02/096868 | 12/2002 |
| WO | 03/051822 | 6/2003 |
| WO | WO 03/066008 | 8/2003 |
| WO | 03/077910 | 9/2003 |
| WO | WO 2006/047466 | 5/2006 |
| WO | 2006/106311 | 10/2006 |
| WO | 2007/123818 | 11/2007 |
| WO | 2007/125818 | 11/2007 |
| WO | WO 2007/127639 | 11/2007 |
| WO | WO 2009/011744 | 1/2009 |
| WO | 2010/096123 | 8/2010 |
| WO | 2010/108012 | 9/2010 |

OTHER PUBLICATIONS

United States Patent Office Action for U.S. Appl. No. 12/138,733 dated Nov. 24, 2009 (10 pages).

United States Patent Office Action for U.S. Appl. No. 12/479,532 dated Oct. 6, 2009 (5 pages).

United States Patent Office Action for U.S. Appl. No. 12/535,513 dated Dec. 18, 2009 (10 pages).

United States Patent Office Action for U.S. Appl. No. 11/174,420 dated Feb. 3, 2010 (6 pages).

Abramovitz, M. et al., "Cloning and expression of a cDNA for the human prostanoid FP receptor," J. Biol. Chem. (1994) 269:2632-2636.

Abramovitz, M. et al., "The utilization of recombinant prostanoid receptors to determine the affinities and selectivities of prostaglandins and related analogs," Biochimica et Biophysica Acta (2000) 1483(2):285-293.

Adis, ADISINSIGHT: ZD-6416, AstraZeneca (United Kingdom) Mar. 27, 2000, 1 page.

AGN-192024, Pharmaprojects, HB4 S1G (2006).

Alm, A., "The potential of prostaglandin derivates in glaucoma therapy; prostaglandins and derivates," Curr. Opin. Opthalmol. (1993) 4(11):44-50.

Alm et al., "Effects on intraocular pressure and side effects of 0.005% latanoprost applied once daily, evening or morning," Ophthalmology (1995) 102(12):1743-1752.

Al-Sereiti, M.R., et al., "Pharmacology of Rosemary (*Rosmarinus Officinalis* Linn.) and Its Therapeutic Potentials," Indian Journal of Experimental Biology, vol. 37, Feb. 1999, pp. 124-130.

Anonymous, "Alprostadil (nexmed):Alprox-TD, Befar, Femprox, Prostaglandin E1 (nexmed)," Drugs R&D (1999) 2(6):413-414.

Audoly, L.P. et al., "Identification of specific EP receptors responsible for the hemodynamic effects of PGE2," Am. J. Physiol. (1999) 46(3):H924-930.

Bartman, W., et al., "Leutolytic Prostaglandins Synthesis and Biological Activity", Prostaglandins, vol. 17, No. 2, pp. 301-311, 1979.

Bundy, G. L., and Lincoln, F. H., "Synthesis of 17-Phenyl-18, 19, 20-Trinoprostaglandins 1. The PG, Series," Prostaglandins, vol. 9, No. 1, (Jan. 1975), pp. 1-4.

Cayatte, a.J. et al., "The thromboxane A2 receptor antagonist S18886 decreases atheroschlerotic lesions and serum intracellular adhesion molecule-1 in the Apo E knockout mouse," Circulation (1998) 96:115.

Chen, J. et al., "AGN 191129: a neutral prostaglandin F-2 alpha (PGF2a) analog that lacks the mitogenic and uterotonic effects typical of FP receptor agonists," IOVS (1999) 40:3562-B420, p. S675.

Chyun, Y.S. et al., "Stimulation of bone formation by prostaglandin E2," Prostaglandins (1984) 27:97-103.

Clissold, D., "The potential for prostaglandin pharmaceuticals," Spec. Publ.—R. Soc. Chem. (1999) 244:115-129.

Coleman, R.A. et al., "Classification of prostanoid receptors: properties, distribution, and structure of the receptors and their subtypes," Pharmacol. Rev. (1994) 46(2):205-229.

Coleman, R.A. et al., "Prostanoids and their receptors," Comprehensive Med. Chem., Membranes and Receptors (1990) 3:643-714.

Collins, P.W. et al., "Synthesis of therapeutically useful prostaglandin and prostacyclin analogs," Chem. Rev. (1993) 93:1533-1564.

Corsini, A. et al., "(5Z)-Carbacyclin discriminates between prostacyclin receptors coupled to adenylate cyclase in vascular smooth muscle and platelets," Br. J. Pharmacol. (1987) 90:255-261.

Dean, T.R. et al., "Improvement of optic nerve head blood flow after one-week topical treatment with travoprost (AL-06221) in the rabbit," IOVS (1999) 40():2688-B563, p. S509.

Delong, M.A., "Prostaglandin receptor ligands: recent patent activity," Drugs (2000) 3(9):1039-1052.

Del Toro, F. et al., "Characterization of prostaglandin E2 receptors and their role in 24,25-(OH)2D2-mediated effects on resting zone chondrocytes," J. Cell Physiol. (2000) 182(2):196-208.

Depperman, W.J., Jr., "Up-to-date scalp tonic," New Eng. J. Med. (1970) 283(2):1115.

Eisenberg, D.L. et al., "A preliminary risk-benefit assessment of latanoprost and unoprostone in open-angle glaucoma and ocular hypertension," Drug Safety (1999) 20(6):505-514.

Ellis, C. K., et al., "Metabolism of Prostaglandin $D_2$ in the Monkey," J. of Biological Chem., vol. 254, No. 10, pp. 4152-4163 (1979).

Fall, P. M., et al. "Inhibition of Collagen Synthesis by Prostaglandins in the Immortalized Rat Osteoblastic Cell Line Pyla: Structure-Activity Relations and Signal Transduction Mechanisms," J. Bone Miner. Res. (1994) 9:1935-1943 (abstract).

Fitzpatrick, F. A., "Separation of Prostaglandins and Thromboxanes by Gas Chromatography with Glass Capillary Columns," Analytical Chemistry, vol. 50, No. 1, pp. 47-52, 1978.

Flisiak, R. et al., "Effect of misoprostol on the course of viral hepatitis B," Hepato-Gastroenterology (1997) 44(17):1419-1425.

Funk, C.D. et al., "Cloning and expression of a cDNA for the human prostaglandin E receptor EP1 subtype," J. Biol. Chem. (1993) 268:26767-26772.

Garadi, R. et al., "Travoprost: a new once-daily dosed prostaglandin for the reduction of elevated intraocular pressure," Iovs (1999) 40(4):4378-B181, p. S831.

Geng, L. et al., "Topical or systemic 16,16 dm-prostaglandin E2 or WR-2721 (WR-1065) protects mice and alopecia after fractionated irradiation," Int. J. Radiat. Biol. (1992) 61(4):533-537.

Geng, L., Malkinson, F.D., Hanson, W.R., "Misoprostol, A PGE1 Analog that is Radioprotective for Murine Intestine and Hair, Induces Widely Different Cytokinetic Changes in these Tissues," Journal of Investigative Dermatology, 1996, vol. 106, No. 4, p. 858.

Griffin, B.W. et al., "Al-8810: a novel prostaglandin F2a analog with selective antagonist effects at the prostaglandin F2a (FP) receptor," J. Pharmacol. Exp. Ther. (1999) 290(3);1278-1284.

Hall, A., Smith, W. H. T., "Clinprost Teijin," Current Opinion in Cardiovascular, Pulmonary & Renal Investigation Drugs, 1999, 1(5), pp. 605-610.

Hallinan, E.A. et al., "Aminoacetyl moiety as a potential surrogate for diacylhydrazine group of SC-51089, a potent PGE2 antagonist, and its analogs," J. Med. Chem. (1996) 39:609-613.

Hanson, W.R. et al., "16,16 dm prostaglandin 2 protects from acute radiation-induced alopecia in mice," Clin. Res. (1988) 36(6):906a.

(56) References Cited

OTHER PUBLICATIONS

Hanson, W.R. et al., "Subcutaneous or topical administration of 16,16 dimethyl prostaglandin E2 protects from radiation-induced alopecia in mice," Int. J. Radiat. Oncol. Biol. Phys. (1992) 23(2):333-337.
Hartke, J.R. et al., "Prostanoid FP agonists build bone in the ovariectomized rat," J. Bone Min. Res. (1999) 14(T326):S207.
Hayashi, M. et al., "Prostaglandin Analogues Possessing Antinidatory Effects. 1. Modification of the ω Chain," J. Med. Chem. (1980) 23(5):519-524.
Hecker, M. et al., "Studies on the interaction of minoxidil with prostacyclin synthase in-vitro," Biochem. Pharmacol. (1988) 37(17):3363-3365.
Houssay, A.B. et al., "Effects of prostaglandins upon hair growth in mice," Acta Physiol. Let. Am. (1976) 266(3):186-191.
Huang, A. et al., "Different modes of inhibition of increase in cytosolic calcium and aggregation of rabbit platelets by two thromboxane A2 antagonists," Asia Pacific Journal of Pharmacology (1994) 9:163-171.
Hulan, H.W. et al., "The development of dermal lesions and alopecia in male rats fed grapeseed oil," Can. J. Physiol. Pharmacol. (1976) 54(1):1-6.
Hulan, H.W. et al., "The effect of long-chain monoenes on prostaglandin E2 synthesis by rat skin," Lipids (1977) 12(7):604-609.
Ichikawa, E.A. et al., "Molecular aspects of the structures and functions of the prostaglandin E receptors," J. Lipid Mediators Cell Signaling (1996) 14:83-87.
Inoue, H., "Thromboxane A2 receptor antagonists," Farumashia (1996) 32(1):1221-1225 (no English translation available).
Jakobsson, P.J. et al., "Membrane-associated proteins in elcosanoid and glutathione metabolism (MAPEG)—a widespread protein superfamily," Am J. Resp. Crit. Care Med. (2000) 161:S20-S24.
Jimenez, J.J. et al., "Stimulated monocyte-conditioned media protect for cytosine arabinoside-induced alopecia in rat," Clin. Res. (1990) 38(4):973a.
Johnstone, M.A., "Hypertrichosis and increased pigmentation of eyelashes and adjacent hair in the region of the ipsilateral eyelids of patients treated with unilateral topical latanoprost," Amer. J. Ophthal. (1997) 544-547.
Johnstone, M.A., Brief latanoprost Rx induces hypertrichosis, IOVS (1998) 39(4):1180-B61.
Karim, S.M.M. et al., "Prostaglandins and human respiratory tract smooth muscle: structure activity relationship," Adv. Prostaglandin Thromboxane Res. (1980) 7:969-980.
Kende, et, al., "Prostaglandin Phosphonic Acids Through Homolytic Halodecarboxylation of Prostaglandins $F_{1\alpha}$ and $F_{2\alpha}$," Tetrahedron Letters, vol. 40, pp. 8189-8192 (1999).
Kerstetter, J.R. et al., "Prostaglandin F2 alpha-l-isopropylester lowers intraocular pressure without decreasing , aqueous humor flow," Am. J. Ophthalmology (1988) 105:30-34.
Kiriyama, M. et al., "Ligand binding specificities of the eight types and subtypes of the mouse prostanoid receptors expressed in Chinese hamster ovary cells," Br. J. Pharm. (1997) 122:217-224.
Kluender, H.C. et al., "The Synthesis of Diethylphosphonoprostaglandin Analogs,," Prostaglandins and Medicine (1979) 2(6):441-444.
Krauss, A.H.P. et al., "Evidence for human thromboxane receptor heterogeneity using a novel series of 9,11-cyclic carbonate derivatives of prostaglandin-F2-alpha," Br. J. Pharmacol. (1996) 117(6):1171-1180.
Kvedar, J.C. et al., "Topical minoxidil in the treatment of male pattern alopecia," Pharmacotherapy (1987) 7(6):191-197.
Lachgar, S. et al., "Effect of VEGF and minoxidil on the production of arachidonic acid metabolites by cultured hair, dermal papilla cells," Eur. J. Dermatol. (1996) 6(5):365-368.
Lachgar, S. et al., "Hair dermal papilla cell metabolism is influenced by minoxidil," Fundam. Clin. Pharmacol. (1997) 11(2):178.
Lachgar, S. et al., "Modulation by minoxidil and VEGF of the production of inflammatory mediators by hair follicle dermal papilla cells," J. Invest. Derm. (1995) 104(1):161.
Lardy, C. et al., "Antiaggregant and antivasospastic properties of the new thromboxane A2 receptor antagonist sodium 4-[[1-[[[(4-chlorophenyl) sulfonyl]amino] methyl] cyclopentyl] methyl] benzeneacetate," Arzneim.-Forsch./Drug Res. (1994) 44(11):1196-1202.
Liljebris, C., Selen, G., Resul, B. Stjernschantz, J., and Hacksell, U., "Derivatives of 17-Phenyl-18, 19, 20 Trinorprostaglan $F_{2\alpha}$ Isopropyl Ester: Potential Antiglaucoma Agents," Journal of Medicinal Chemistry, vol. 38, No. 2, (1995), pp. 289-304.
Ling, G. et al., "16,16 dm prostaglandin E2 protects mice fiorn fractionated radiation-induced alopecia," Clin. Res. (1990) 38(3):858a.
Lundy, M.W. et al., "Restoration of cancellous architecture and increased bone strength in aged osteopenic rats treated with fluprostenol, "J. Bone Min. Res. (1999) 1(4)SA368:S401.
Malkinson, F.D. et al., "Prostaglandins protect against murine hair injury produced by ionizing radiation or doxorubicin," J. Invest. Dermatol. (1993) 101(1, Suppl):135S-137S.
Maruyama, T. et al., "EP1 receptor antagonists suppress tactile allodynia in rats," Prostaglandins Lipid Mediat. (1999) 59:217.
Matsumura, H., "Prostaglandins and Sleep," Saishin No to Shinkai Kagaku Shiritzu 10, 1998, pp. 79-89 (no English translation available).
Maw, G.N., "Pharmacological therapy for the treatment of erectile dysfunction," Annu. Rep. Med. Chem. (1999) 34:71-80.
Mccullough, P.A., "Ridogrel,"Current Opinion in Anti-inflammatory & Immunomodulatory Investigation Drugs (1999) 1(3):265-276.
Michelet, J.F. et al., "Activation of cytoprotective prostaglandin synthase-1 by minoxidil as a possible explanation for its hair growth-stimulation effect," J. Invest. Dermatol. (1997) 108(2):205-209.
Mihele, D., "The Testing of the Hepatoprotective Action of Some New Synthetic Prostaglandins," Farmacia (Bucharest) vol. 47 (5), 1999, pp. 43-58 (Abstract in English).
Millikan, L.E., "Treatment of alopecia," J. Clin. Pharmacol. (1987) 27(9):715.
Millikan, L.E., "Treatment of male pattern baldness," Drug Therapy (1989) 19(3):62-73.
Miyamoto, T., et al., "A comparison in the Efficacy and Safety between Ramatroban (Bay u 3405) and Ozargrel HC1 for Bronchial Asthma: A Phase III, Multi-Center, Randomized, Double-Blind, Group Comparative Study," 13, 1997, pp. 599-639 Abstract (in English).
Mori, S. et al., "Effects of prostaglandin E2 on production of new cancellous bone in the axial skeleton of overlectomized rats," Bone (1990) 11:103-113.
Murakami, T. et al., "Effect of isocarbacyclin methyl ester incorporated in lipid microspheres on experimental models of peripheral obstructive disease," Arzheim.-Forsh/Drug Res. (1995) 45(II)(9):991-994.
Narumiya, S., "Roles of prostanoids in health and disease, lessons from receptor-knockout mice," Int. Congr. Ser. (1999) 1181:261-269.
Negishi, M. et al., "Molecular mechanisms of diverse actions of prostanoid receptors," Biochimica et Biophysica Acta (1995) 1259:109-120.
Norridin, R.W. et al., "The role of prostaglandins in bone in vivo," Prostaglandins, Leukotrienes and Essential Fatty Acids (1990) 41:139-149.
Olsen, E.A. et al., "Transdermal viprostol in the treatment of male pattern baldness," J. Amer. Acad. Dermatol. (1990) 23(3 Part 1):470-472.
Orlicky, D.J., "Negative regulatory activity of a prostaglandin F2a receptor associated protein (Fprp)," Prostaglandins, Leukotrienes and Essential Fatty Acids (1996) 54(4):247-259.
Phamaprojects, No. 6321, Merck & Co. (2006) 1 page.
Rampton, D.S., Carty, E., Van Nueten, L., Anti-Inflammatory Profile in Vitro of Ridogrel, a Putative New Treatment for Inflammatory Bowel Disease, Gastroenterology, 1999, (116) G3477, p. 801.
Roenigk, H.H., "New topical agents for hair growth," Clinics in Dermatology (1988) 6(4):119-121.
Roof, S.L. et al., "mRNA expression of prostaglandin receptors EP1, EP2, EP3 and EP4 in human osteoblast-like cells and 23 human tissues," J. Bone Mm. Res. (1996) 11:S337.

(56) References Cited

OTHER PUBLICATIONS

Ruel, R. et al., "New class of biphenylene dibenzazocinones as potent ligands for the human EP1 prostanoid receptor," Bioorg. Med. Chem. Lett. (1999) 9:2699-2704.
Sakuma, Y. et al., "Crucial involvement of the PE4 subtype of prostaglandin E receptor in osteoclast formation by proinflammatory cytokines and lipopolysaccharide," J. Bone Min. Res. (2000) 15(2):218-227.
Sauk, J.J. et al., "Influence of prostaglandin E-1 prostaglandin E-2 and arachidonate on melanosomes in melanocytes and keratinocytes of anagen bulbs in-vitro," J. Invest. Dermatol. (1975) 64(5):332-337.
Sharif; N.A. et al., "3H Al-5848 ([3H]9 beta-(+)-fluprostenol). Carboxylic acid of travoprost (AL-6221), a novel FP prostaglandin to study the pharmacology and autoradiographic localization of the FP receptor," J. Phar. Pharmacol. (1999) 51(6):685-694.
Shih, M.S. et al., "PGE2 induces regional remodeling changes in Haversian envelope: a histomorphometric study of fractured ribs in beagles," Bone and Mineral (1986) 1:227-234.
Shimazaki, A., et al. "New Ethacrynic Acid Derivatives as Potent Cytoskeletal Modulators in Trabecular Meshwork Cells," Biol. Pharm. Bull. vol. 27, No. 6, 2004, pp. 846-850.
Shimazaki, A., et al., "Effects of the New Ethacrynic Acid Derivative SA9000 on Intraocular Pressure in Cats and Monkeys," Biol Pharm. Bull. vol. 27, No. 7, 2004, pp. 1019-1024.
Souillac, P. et al., "Characterization of delivery systems, differential scanning calorimetry," Encyclopedia of Controlled Drug Delivery, John Wiley & Sons (1999) 212-227.
Sredni, B. et al., "The protective role of the immunomodulator AS101 against chemotherapy-induced alopecia studies on human and animal models," Int. J. Cancer (1996) 65(1):97-103.
Tereda, N. et al., "Effect of a thromboxane A2 receptor antagonist, ramatroban (Bay U3405), on inflammatory cells, chemical mediators and non-specific nasal hyperactivity after allergen challenge in patients with perennial allergic rhinitis," Allergology Int. (1998) 47(1):59-67.
Tomita, Y. et al., "Melanocyte-stimulating properties of arachidonic acid metabolites: possible role in postinflammatory pigmentation," Pigm. Cell Res. (1992) 5(5, Pt. 2):357-361.
Ueda, K. et al., "Brief clinical and laboratory observations: coritical hyperostosis following long-term administration of prostaglandin El in infants with cyanotic congenital heart disease," J. Pediatrics (1980) 97:834-836.
Vandenburgh, A.M. et al., "A one-month dose-response study of AGN 192024, a novel antiglaucoma agent, in patients with elevated intraocular pressure," IOVS (1999) 40(4):4373-B176, p. S830.
Vayssairat, M., Preventive Effect of an Oral Prostacyclin Analog, Beraprost Sodium, on Digital Necrosis in Systemic Scierosis, J. of Rheumatol., 1999, 26(10), pp. 2173-2178.
Vengerovsky, A.I. et al., "Hepatoprotective action of prostaglandins," Eksp. Klin. Farmakof. (1997) 60(5):78-82.
Verbeuren, T., et al., "The TP-Receptor Antagonist S 18886 Unmasks Vascular Relaxation and Potentiates the Anti-Platelet Action of $PGD_2$," Journal of the International Society Thrombosis and Haemostasis, Jun. 6-12, 1997, p. 693.
Vincent, J.E., "Prostaglandin synthesis and selenium deficiency a hypothesis," Prostaglandins (1974) 8(4):339-340.
Vippagunta, "Crystalline solids," Adv. Drug Del. Rev. (2001) 48:3-26.
Voss, N. G. et al., "Induction of anagen hair growth in telogen mouse skin by topical latanoprost application," IOVS (1999) 40:3570-B428, p. S676.
Waddell, K. A., et al., "Combined Capillary col. Gas Chromatography Negative Ion Chemical Ionization Mass Spectrometry of Prostanoids," Biomed. Mass Spectrom., vol. 10, No. 2, pp. 83-88 (1983).
Wang, Y. et al., "The design and synthesis of 13, 14-dihydro prostaglandin F1a analogs as potent and selective ligands for the human FP receptor," J. Med. Chem. (2000) 43(5):945-952.
Watson et al., "A six-month, randomized, double-masked study in comparing latanoprost with timolol in open-angle glaucoma and ocular hypertension," Ophthalmology (1996) 103:126-137.
Woodward, D.F. et al., "Emerging evidence for additional prostanoid receptor subtypes," Curr. Top. Pharmacol. (1998) 4:153-163.
Woodward, D.F. et al., "Molecular characterization and ocular hypotensive properties of the prostanoid EP2 receptor," J. Oc. Pharm. Therap. (1995) 11(3):447-454.
Woodward, D.F. et al., "Studies on the ocular effects of a pharmacologically novel agent prostaglandin F2 alpha 1-OCH3 (AGN 191129) N-S," Arch. Pharmacol. (1998) 358(1):P1713.
Yoshida, K. et al., "Synthesis and pharmacological activities of the new TXA2 receptor antagonist Z-335 and related compounds," AFMC (1995) 95:53.
Zimbric, M.L. et al., "Effects of latanoprost of hair growth in the bald scalp of stumptailed macaques," IOVS (1999) 40:3569-B427, p. S676.
International Search Report for Application No. PCT/US00/05301 dated Jul. 21, 2000 (3 pages).
Written Opinion for Application No. PCT/US00/05301 dated Oct. 20, 2000 (7 pages).
International Preliminary Examination Report for Application No. PCT/US00/05301 dated Mar. 16, 2001 (6 pages).
International Search Report for Application No. PCT/US00/20851 dated Nov. 7, 2000 (4 pages).
Written Opinion for Application No. PCT/US00/20851 dated Jul. 10, 2001 (9 pages).
International Preliminary Examination Report for Application No. PCT/US00/20851 dated Oct. 12, 2001 (8 pages).
International Search Report for Application No. PCT/US98/18339 dated Dec. 3, 1998 (2 pages).
International Preliminary Examination Report for Application No. PCT/US98/18339 dated Jun. 28, 1999 (4 pages).
International Search Report for Application No. PCT/US98/18340 dated Dec. 8, 1998 (3 pages).
Written Opinion for Application No. PCT/US98/18340 dated Aug. 2, 1999 (7 pages).
International Preliminary Examination Report for Application No. PCT/US98/18340 dated Dec. 6, 1999 (7 pages).
International Search Report for Application No. PCT/US98/18594 dated Dec. 3, 1998 (3 pages).
Written Opinion for Application No. PCT/US98/18594 dated May 25, 1999 (5 pages).
International Preliminary Examination Report for Application No. PCT/US98/18594 dated Sep. 7, 1999 (5 pages).
International Search Report for Application No. PCT/IB99/00478 dated Jul. 12, 1999 (3 pages).
Written Opinion for Application No. PCT/IB99/00478 dated Feb. 21, 2004 (4 pages).
International Preliminary Examination Report for Application No. PCT/IB99/00478 dated Jun. 23, 2000 (5 pages).
International Search Report for Application No. PCT/IB99/00480 dated Jun. 25, 1999 (3 pages).
Written Opinion for Application No. PCT/IB99/00480 dated Jan. 18, 2000 (6 pages).
International Search Report for Application No. PCT/US00/05299 dated Jul. 28, 2000 (3 pages).
Written Opinion for Application No. PCT/US00/05299 dated Oct. 20, 2000 (7 pages).
International Preliminary Examination Report for Application No. PCT/US00/05299 dated Mar. 16, 2001 (7 pages).
International Search Report for Application No. PCT/US01/10368 dated Nov. 7, 2001 (3 pages).
International Preliminary Examination Report for Application No. PCT/US01/10368 dated Jun. 14, 2002 (2 pages).
International Search Report for Application No. PCT/US01/10369 dated Nov. 7, 2001 (3 pages).
International Preliminary Examination Report for Application No. PCT/US01/10369 dated Jun. 14, 2001 (3 pages).
International Search Report for Application No. PCT/US01/10370 dated Nov. 7, 2001 (3 pages).
International Preliminary Examination Report for Application No. PCT/US01/10370 dated Jun. 14, 2002 (2 pages).

(56) References Cited

OTHER PUBLICATIONS

International Search Report for Application No. PCT/US01/10547 dated Jan. 2, 2002 (2 pages).
International Preliminary Examination Report for Application No. PCT/US01/10547 dated Jun. 14, 2002 (2 pages).
United States Patent Office Action for U.S. Appl. No. 12/479,532 dated Apr. 22, 2010 (6 pages).
United States Patent Office Notice of Allowance for U.S. Appl. No. 12/138,733 dated Jun. 3, 2010 (5 pages).
United States Patent Office Action for U.S. Appl. No. 11/476,246 dated Apr. 19, 2010 (7 pages).
United States Patent Office Notice of Allowance for U.S. Appl. No. 12/535,513 dated Jun. 3, 2010 (5 pages).
United States Patent Office Action for U.S. Appl. No. 11/334,689 dated Apr. 30, 2010 (11 pages).
United States Office Action for U.S. Appl. No. 09/946,021 dated Jan. 15, 2002 (5 pages).
United States Office Action for U.S. Appl. No. 09/946,021 dated May 24, 2002 (4 pages).
United States Office Action for U.S. Appl. No. 09/946,021 dated Oct. 15, 2002 (4 pages).
United States Office Action for U.S. Appl. No. 11/174,420 dated Aug. 20, 2007 (8 pages).
United States Office Action for U.S. Appl. No. 11/174,420 dated Dec. 5, 2008 (6 pages).
United States Office Action for U.S. Appl. No. 11/174,420 dated Jul. 22, 2009 (5 pages).
United States Office Action for U.S. Appl. No. 09/148,006 dated Jan. 29, 1999 (3 pages).
United States Office Action for U.S. Appl. No. 09/148,374 dated Feb. 11, 1999 (4 pages).
United States Office Action for U.S. Appl. No. 09/148,374 dated May 28, 1999 (3 pages).
United States Office Action for U.S. Appl. No. 09/148,374 dated Oct. 1, 1999 (3 pages).
United States Office Action for U.S. Appl. No. 09/148,374 dated Jan. 10, 2000 (4 pages).
United States Office Action for U.S. Appl. No. 09/148,538 dated Apr. 8, 1999 (6 pages).
United States Office Action for U.S. Appl. No. 09/647,381 dated Sep. 20, 2001 (8 pages).
United States Office Action for U.S. Appl. No. 09/647,380 dated Sep. 18, 2001 (8 pages).
United States Office Action for U.S. Appl. No. 09/914,531 dated Dec. 7, 2001 (5 pages).
United States Office Action for U.S. Appl. No. 09/774,555 dated Jul. 9, 2002 (8 pages).
United States Office Action for U.S. Appl. No. 09/774,555 dated May 23, 2005 (7 pages).
United States Office Action for U.S. Appl. No. 09/774,555 dated Jan. 6, 2006 (6 pages).
United States Office Action for U.S. Appl. No. 09/774,555 dated Aug. 31, 2006 (9 pages).
United States Office Action for U.S. Appl. No. 11/565,297 dated Jul. 12, 2007 (5 pages).
United States Office Action for U.S. Appl. No. 11/565,297 dated Jul. 31, 2007 (5 pages).
United States Office Action for U.S. Appl. No. 09/774,558 dated Apr. 25, 2002 (13 pages).
United States Office Action for U.S. Appl. No. 09/774,558 dated Apr. 15, 2003 (11 pages).
United States Office Action for U.S. Appl. No. 09/774,558 dated Dec. 4, 2003 (11 pages).
United States Office Action for U.S. Appl. No. 09/774,558 dated Nov. 5, 2004 (6 pages).
United States Office Action for U.S. Appl. No. 09/774,558 dated Mar. 28, 2006 (8 pages).
United States Office Action for U.S. Appl. No. 11/476,246 dated Jul. 22, 2009 (9 pages).
United States Office Action for U.S. Appl. No. 09/774,557 dated Mar. 5, 2003 (9 pages).
United States Office Action for U.S. Appl. No. 09/774,557 dated Nov. 26, 2004 (10 pages).
United States Office Action for U.S. Appl. No. 11/138,097 dated Jul. 16, 2007 (1 pages).
United States Office Action for U.S. Appl. No. 11/967,423 dated Feb. 4, 2009 (10 pages).
United States Office Action for U.S. Appl. No. 09/774,556 dated Mar. 19, 2002 (11 pages).
United States Office Action for U.S. Appl. No. 09/774,556 dated May 14, 2003 (2 pages).
United States Office Action for U.S. Appl. No. 09/774,556 dated Mar. 23, 2004 (10 pages).
United States Office Action for U.S. Appl. No. 09/774,556 dated Dec. 14, 2004 (5 pages).
United States Office Action for U.S. Appl. No. 09/774,556 dated Jul. 18, 2005 (6 pages).
United States Office Action for U.S. Appl. No. 11/334,689 dated Aug. 25, 2009 (11 pages).
United States Patent Office Action for U.S. Appl. No. 12/138,733 dated Feb. 23, 2011 (8 pages).
United States Patent Office Notice of Allowance for U.S. Appl. No. 11/174,420 dated Jan. 12, 2011 (5 pages).
U.S. Appl. No. 90/009,430, filed Mar. 15, 2009, Woodward.
U.S. Appl. No. 90/009,431, filed Mar. 10, 2009, Johnstone.
"Agents for Glaucoma," Journal of the American Pharmaceutical Association, New Drugs of 2001, http://www.edscape.com/viewarticle/436631_22 (2007) 4 pages.
"Bimatoprost (ophthalmic)" Medlineplus, Health information online (Jul. 24, 2001) 4 pages, www.nlm.nih.gov/medlineplus/druginfor/uspdi/500295.
Letter from Bernice Tao at Apotex, Inc. to the General Counsels at Allergan, Inc. and Duke University regarding "Apotex Bimatoprost Topical Solution 0.03% Paragraph IV Certification—U.S. Patent Nos. 7,351,404 and 7,388,029" (Jul. 26, 2010) 49 pages.
Allergan Press Release, "Phase III Lumigan? (AGN 192024) data presented at American Academy of Ophthalmology," Mar. 1, 2000, 5 pages.
Alm, A. et al., "Phase III latanoprost studies in Scandanavia, the United Kingdom and the United States," Surv. Ophthalmol. (1997) 41(Suppl 2):S105-S110.
Alm, A. et al., "Uveoscleral outflow—a review," Exp. Eye Res. (2009) 88(4):760-768, Epub Jan. 3, 2009.
Bean, G.W., "Commercially available prostaglandin analogs for the reduction of intraocular pressure: similarities and differences," Survey of Ophthalmology (2008) 53(1):S69-84.
Berglund, B.A. et al., "Investigation of structural analogs of prostaglandin amides for binding to and activation of CB1 and CB2 cannabinoid receptors in rat brain and human tonsils," Adv. Exp. Med. Biol. (1999) 469:527-533.
Bito, L., "A new approach to the medical management of glaucoma, from the bench to the clinic, and beyond," The Proctor Lecture (2001) 42(6):1126-1133.
Bito, L.Z. et al., "Long-term maintenance of reduced intraocular pressure by daily or twice daily topical application of psotaglandins to cat or rhesus monkey eyes," Invest. Ophthalmol. Vis. Sci. (1983) 24(3):312-319.
Brandt, J.D. et al., "Comparison of once-or twice-daily bimatoprost with twice-daily timolol in pateints with elevated IPO. A three month clinical tril," Ophthalmology (2001) 108(6):1023-1031.
Cadet, P. et al., "Molecular identification and functional expression of mu3, a novel alternatively apliced variant of the human mu opiate receptor gene," J. Immunol. (2003) 170(10):5118-5123.
Camras, C.B. et al., "Latanoprost, a prostaglandin analog, for glaucoma therapy," Ophthalmology (1996) 103(11):1916-1924.
Camras, C.B. et al., "Multiple dosing of prostaglandin F2alpha or epinephrine on cynomolgus monkey eyes," Invest. Ophthalmol. Vis. Sci. (1987) 28(3):463-469.
Camras, C.B. et al., "Multiple dosing of prostaglandin F2alpha or epinephrine on cynomolgus monkey eyes," Invest. Ophthalmol. Vis. Sci. (1988) 29(9):1428-1436.

(56) References Cited

OTHER PUBLICATIONS

Camras, C.B. et al., "Reduction of intraocular pressure in normal and glaucomatous primate (*Aotus trivirgatus*) eyes by topically applied prostaglandin F2alpha," Curr. Eye Res. (1981) 1(4):205-209.
Camras, C.B. et al., "Multiple dosing of prostaglandin F2alpha or epinephrine on cynomolgus monkey eyes," Invest. Ophthalmol. Vis. Sci. (1987) 28(6):921-926.
Camras, C.B. et al. "Bimatoprost, the prodrug of a prostaglandin analogue," Br. J. Ophthalmol. (2008) 92:862-863.
Camras, C.B., "Comparison of latanoprost and timolol in patients with ocular hypertension and glaucoma," Ophthalmology (1996) 103(1):138-147.
Camras, C.B., "Detection of the free acid of bimatoprost in aqueous humor samples from human eyes treated with bimatoprost before cataract surgery," American Academy of Ophthalmology (2004) 2193-2198.
Cantor, L.B. et al., "Levels of bimatoprost acid in the aqueous humour after bimatoprost treatment of patients with cataract," Br. J. Ophthalmol. (2007) 91:629-632.
Cantor, L.B., "Reply—bimatoprost, the prodrug of a prostaglandin analogue," Br. J. Ophthalmol. (2008) 92:863-864.
CAS RN 155206-00-1 (May 20, 1994).
Center for Drug Evaluation and Research, "Medical Officer's Review of NDA, Application No. 21-275," Mar. 14, 2001; 120-day safety update Jan. 23, 2001; Mar. 2, 2001; Sep. 18, 2000, 63 pages.
Crowston, J.G. et al., "Effect of bimatoprost on intraocular pressure in prostaglandin FP receptor knockout mice," Invest. Ophthal. Vis. Sci. (2005) 46:4571-4577.
Darnell, J. et al., "Cell-to-cell signaling: hormones and receptors," Mol. Cell. Biol. (1990) 738-743.
Davies, S.S., "Hydrolysis of bimatoprost (lumigan) to its free acid by ocular tissue in vitro," J. Ocular Pharm. Thera. (2003) 19(1):45-54.
DuBINER, H. et al., "Efficacy and safety of bimatoprost in patients with elevated intraocular pressure: a 30-day comparison with latanoprost," Survey of Ophthal. (2001) 45(S4):S353-S360.
Fagot, D. et al., "Mitogenic signaling by prostaglandins in chemically transformed mouse fibroblasts: comparison with phorbol esters and insulin," Endocrinology (1993) 132(4):1729-1734.
Faulkner, R., "Aqueous humor concentrations of bimatoprost free acid, bimatoprost and travoprost free acid in cataract surgical patients administered multiple topical ocular doses of Lumigan® or Travatan®," J. Ocular Pharm. Thera. (2010) 26(2):147-156.
FDA Label for Approved NDA 22-184—Lumigan 0.01% and Lumigan 0.03% (Aug. 31, 2010) 5 pages.
FDA Press Release, "FDA News" of Mar. 16, 2001 entitled "FDA approves two new intraocular pressure lowering drugs for the management of glaucoma," 2 pages.
Fiscella, R.G., "Peek into the drug pipeline," Review of Optometery Online, Jan. 15, 2001, pp. 1-5.
Frenkel, R.E. et al., "Evaluation of circadian control of intraocular pressure after a single drop of bimatoprost 0.03% or travoprost 0.004%," Curr. Med. Res. Opin. (2008) 24(4):919-923, epub Feb. 8, 2008.
Gandolfini, S. et al., "Three-month comparison of bimatoprost and latanoprost in patients with glaucoma and ocular hypertension," Adv. In Therapy (2001) 18(3):110-121.
Gerth, J. et al., "Drug makers reap profits on tax-backed research," New York Times, Apr. 23, 2000, 10 pages.
Giuffre, G., "The effects of prostaglandin F2alpha in the human eye," Graefe's Arch. Clin. Exp. Ophthalmol. (1985) 222:139-141.
Hellberg, M.R. et al., "The hydrolysis of the prostaglandin analog prodrug bimatoprost to 17-phenyltrinor PGF2a by human and rabbit ocular tissue," J. Ocular Pharmacol. Ther. (2003) 19:97-103.
Jimenez De Asua, L. et al., "The stimulation of the initiation of DNA synthesis and cell division in Swiss mouse 3T3 cells by prostaglandin F2alpha requires specific functional groups in the molecule," J. Biol. Chem. (1983) 256(14): 8774-8780.
Jordan, B.A. et al., "G-protein coupled receptor heterodimerization modulates receptor function," Nature (1999) 399(6737):697-700.
Kaufman, P.L., "Effects of intracamerally infused prostaglandins on outflow facility in cynomolgus monkey eyes with intact or retrodisplaced ciliary muscle," Exp. Eye Res. (1986) 43:819-827.
Lee, P.-Y. et al., "The effect of prostaglandin F2alpha on intraocular pressure in mormotensive human subjects," Invest. Ophthalmol. Vis. Sci. (1988) 29(10):1474-1477.
Liang, Y. et all., "Identification and pharmacological characterization of the prostaglandin FP receptor and FP receptor varian complexes," Br. J. Pharmacol. (2008) 154:1079-1093.
Lumigan 6-month phase 3 data presented at American Glaucoma Society Meeting, Mar. 2, 2001, Business Wire, 3 pages.
Maxey, K.M., "The hydrolysis of bimatoprost in corneal tissue generates a potent prostanoid FP receptor agonist," Survey of Ophthalmology (2002) 47(1):S34-40.
Mishima, H.K. et al., "A comparison of latanoprost and timolol in primary open-angle glaucoma and ocular hypertension," Arch. Ophthalmol. (1996) 114:929-932.
Ortonne, J-P. et al., "Hair melanin's and hair color: ultrastructural and biochemical aspects," J. Soc. Inv. Derm. (1993) 82S-89S.
Pfeiffer, N., "New developments in glaucoma drug therapy," Ophthalmologist (1992) 89:W1-W13.
Poyer, J.F. et al., "Prostaglandin F2 alpha effects on isolated rhesus monkey ciliary muscle," Invest. Ophthalmol. Vis. Sci. (1995) 36(12):2461-2465.
Response from the Food and Drug Administration to Pfizer's Citizen Petition and a Supplement (Aug. 31, 2010) at 23 (Exhibit 5) Regarding Docket No. FDA-2006-P-0072, 26 pages.
Resul, B. et al., "Phenyl-substituted prostaglandins: potent and selective antiglaucoma agents," J. Med. Chem. (1993) 36(2):243-248.
Romano, M.R., "Evidence for the involvement of cannabinoid CB1 receptors in the bimatoprost-induced contractions on the human isolated ciliary muscle," Invest. Opthal. Vis. Sci. (2007) 48(8):3677-3682.
Sharif, N.A. et al., "Bimatoprost and its free acid are prostaglandin FP receptor agonists," Eur. J. Pharmacol. (2001) 432(2-3):211-213.
Sharif, N.A. et al., "Cat iris sphincter smooth-muscle contraction: comparison of FP-class prostaglandin analog agonist activities," J. Ocul. Pharmacol. Ther. (2008) 24(2):152-163.
Sharif, N.A. et al., "Human ciliary muscle cell responses to FP-class prostaglandin analogs: phosphoinositide hydrolysis, intracellular Ca2+ mobilization and MAP kinase activation," J. Ocul. Pharmacol. Ther. (2003) 19:437-455.
Sharif, N.A. et al., "Human trabecular meshwork cell responses induced by bimatoprost, travoprost, unoprostone, and other FP prostaglandin receptor agonist analogues," Invest. Ophthalmol. Vis. Sci. (2003) 44:715-721.
Sharif, N.A., "Ocular hypotensive FP prostaglandin (PG) analogs: PG receptor subtype binding affinities and selectivities, and agonist potencies at FP and other PG receptors in cultured cells," J. Ocular Pharm. Thera. (2003) 19(6):501-515.
Sharif, N. A., "Update and commentary on the pro-drug bimatoprost and a putative 'prostamide receptor'," Expert Rev. Ophthalmol. (2009) 4(5):477-489.
Sherwood, M. et al., "Six-month comparison of bimatoprost once-daily and twice-daily with timomol twice-daily in patients with elevated intraocular pressure," Surv. Ophthal. (2001) 45(4):S361-S368.
Sjoquist, B. et al., "Ocular and systemic pharmacokinetics of latanoprost in humans," Surv. Ophthalmol. (2002) 47(Supp 1):S6-12.
Sjoquist, B. et al., "Pharmacokinetics of latanoprost in the cynomolgus monkey. 3rd communication: tissue distribution after topical administration on the eye studied by whole body autoradiography, Glacoma research laboratories," Arzneimittelforschung (1999) 49:240-249.
Spada, C.S. et al., "Bimatoprost and prostaglandin F(2 alpha) selectively stimulate intracellular calcium signaling in different cat iris sphincter cells," Exp. Eye Res. (2005) 80(1):135-145.
Stamer, W.D. et al., "Cellular basis for bimatoprost effects on human conventional outflow," Invest. Ophthalmol. Vis. Sci. (2010) 51(10):5176-5181, Epub Apr. 30, 2010.
Stjernschantz, J. et al., "Phenyl substituted prostaglandin analogs for glaucoma treatment," Drugs of the Future (1992) 17(8):691-704.

(56) References Cited

OTHER PUBLICATIONS

Stjernschantz, J., "Studies on ocular inflammation and development of a prostaglandin analogue for glaucoma treatment," Exp. Eye Res. (2004) 78(4):759-766.
Stjernschantz, J.W., "From PGF2alpha-isopropyl ester to latanoprost: a review of the development of Xalatan: the Proctor lecture," Invest. Ophthalmol. Vis. Sci. (2001) 42(6):1134-1145.
The Newsletter of the Glaucoma Foundation, Fall 2000, vol. 11, No. 2, 11 pages.
Van Alphen, G.W.H.M. et al., "The effect of prostaglandins on the isolated internal muscles of the mammalian eye, including man," Documenta Ophthalmologica (1977) 42(2):397-415.
Vielhauer, G.A. et al., "Cloning and localization of hFP(S): a six-transmembrane mRNA splice variant of the human FP prostanoid receptor," Arch. Biochem. Biophys. (2004) 421(2):175-185.
Villumsen, J. et al., "Prostaglandin F2alpha-isopropylester eye drops: effect on intraocular pressure in open-angle glaucoma," Br. J. Ophthalmol. (1989) 73:975-979.
White, J.H. et al., "Heterodimerization is required for the formation of a functional GABA(B) receptor," Nature (1998) 396(6712):679-682.
Wilson, S.J. et al., "Dimerization of the human receptors for prostacyclin and thromboxane facilitates thromboxane receptor-mediated cAMP generation," J. Biol. Chem. (2004) 279(51):53036-53047.
Woodward, D., "Replacement of carboxylic acid group of prostaglandin F2a with a hydroxyl or methoxy substituent provides biologically unique compounds," Br. J. Pharma. (2000) 130(8):1933-1943.
Woodward, D.F. et al., "Bimatoprost effects on aqueous humor dynamics in monkeys," J. Ophthalmol. (2010) Article ID 926192, 5 pages.
Woodward, D.F. et al., "Bimatoprost: a novel antiglaucoma agent," Cardiovasc. Drug Rev. (2004) 22(2):103-120.
Woodward, D.F. et al., "Identification of an antagonist that selectively blocks the activity of prostamides (prostaglandin-ethanolamides) in the feline iris," Br. J. Pharmacol. (2007) 150:342-352.
Woodward, D.F. et al., "Pharmacological characterization of a novel anti-glaucoma agent," J. Pharmacol. Exp. Ther. (2003) 305:772-785.
Woodward, D.F. et al., "The pharmacology of bimatoprost (Lumigan)," Surv. Ophthalmol. (2001) 45(Suppl 4):S337-45.
Yamaji, K. et al., "Prostaglandins El and E2, but not F2alpha or latanoprost, inhibit monkey ciliary muscle contraction," Curr. Eye Res. (2005) 30(8):661-665.
Zeigler, T., "Old drug, new use: new research shows common cholesterol-lowering drug reduces multiple sclerosis symptoms in mice," Natl. Institute of Neurological Disorders and Stroke (2003) 2 pages.
United States Patent Office Action for U.S. Appl. No. 12/535,513 dated Mar. 3, 2011 (8 pages).
"Phase III lumigan—AGN 192024—data presented at American Academy of Ophthalmology," Business Wire (Oct. 23, 2000) 3 pages.
Brubaker, R.F. et al., "Effects of AGN 192024, a new ocular hypotensive agent, on aqueous dynamics," Am. J. Opthal. (2001) 131(1):19-24.
Mansberger, S.L. et al., "Eyelash formation secondary to latanoprost treatment in a patient with alopecia," Arch. Ophthalmol. (2000) 118:718-719.
Invitation to Pay Additional Fees and Partial International Search for Application No. PCT/US2009/062590 dated Aug. 19, 2010 (5 pages).
International Search Report and Written Opinion for Application No. PCT/US2009/062590 dated Nov. 16, 2010 (16 pages).
Invitation to Pay Additional Fees and Partial International Search for Application No. PCT/US2010/43701 dated Sep. 28, 2010 (2 pages).
International Search Report and Written Opinion for Application No. PCT/US2010/43701 dated Dec. 7, 2010 (10 pages).
International Search Report and Written Opinion for Application No. PCT/US2010/27831 dated Apr. 26, 2010 (8 pages).
United States Patent Office Action for U.S. Appl. No. 12/479,532 dated Oct. 28, 2010 (5 pages).
United States Patent Office Action for U.S. Appl. No. 11/476,246 dated Sep. 14, 2010 (3 pages).
United States Patent Office Action for U.S. Appl. No. 12/260,534 dated Nov. 18, 2011 (8 pages).
United States Patent Office Notice of Allowance for U.S. Appl. No. 12/479,532 dated Dec. 16, 2011 (4 pages).
United States Patent Office Notice of Allowance for U.S. Appl. No. 12/260,534 dated Feb. 21, 2013 (11 pages).
European Patent Office Action for Application No. 09748621.1 dated Jan. 16, 2013 (6 pages).
Allergan Clinical Study Report, Study No. 192024-008, "A multicenter, double-masked, unevenly randomized, parallel, active-controlled three-month study (with treatment extended to one year) of the safety and efficacy of once-daily or twice-daily administered AGN 192024 0.03% ophthalmic solution compared with twice-daily administered timolol 0.5% ophthalmic solution in subjects with glaucoma or ocular hypertension," (Aug. 1, 2000), vol. 1 of 32, 356 pages.
Allergan Clinical Study Report, Study No. 192024-009, "A multicenter, double-masked, randomized, parallel, 3-month study (with treatment extended to 1 year) of the safety and efficacy of AGN 192024 0.03% ophthalmic solution administered once-daily or twice-daily compared with Timolol 0.5% ophthalmic solution administered twice-daily in subjects with glaucoma or ocular hypertension" (Aug. 2, 2000) 34 pages.
Allergan Clinical Study Report, Study No. 192024-010-01, "A multicenter, investigator-masked, randomized, parallel study of the safety and efficacy of AGN 192024 0.03% ophthalmic solution compared with Latanoprost 0.005% ophthalmic solution administered once-daily in subjects with glaucoma or ocular hypertension" (May 9, 2001) 38 pages.
Bialer, M. et al., "Pharmacokinetics of valpromide after oral administration of a solution and a tablet to healthy volunteers," Eur. J. Clin. Pharma. (1984) 27:501-503.
Bito, L.Z. et al., "The ocular pharma-cokinetics of eicosanoids and their derivatives," Exp. Eye Res. (1987) 44:217-226.
Bockaert, J. et al., "Molecular tinkering of G protein-coupled receptors: an evolutionary success," Eur. Molecular Biol. Org. (1999) 18:1723-1729.
Brown, M.M. et al., "Improper topical self-administration of ocular medication among patients with glaucoma," Can. J. Ophthal. (1984) 19(1):2-5.
Buck, F. et al., "Characterization of N- and C-terminal deletion mutants of the rat serotonin HT2 receptor in *xenopus laevis* oocytes," Biochem. Biophys. Res. Comm (1991) 178, 1421-1428.
Camras, C.B. et al., "Reduction of intraocular pressure by prostaglandins applied topically to the eyes of conscious rabbits," Invest. Ophthal & Vis. Sci. (1977) 16, 1125-1134.
Chen, J. et al., "Replacement of the carboxylic acid group of prostaglandin F2alpha (PGH2alpha) with certain non-ionizable substituents results in pharmacologically unique ocular hypotensive agents," 11th International Conference Advances Prostaglandins and Leuotremic Res. Basic Sci. & New Clinical Applications—Abstract book (2000) 48.
Chen, J. et al., "Structure-based dissociation of a type I polyketide synthase module," Chem. Biol. (2007) 14, 784-792.
Chen, J. et al., "Studies on the pharmacology of prostamide F2alpha a naturally occurring substance," Br. J. Pharm. (2001) 133, 63p.
Chen, J. et al., "Studies using isolated uterine and other preparations show Bimatoprost and prostanoid FP agents have different activity profiles," Br. J. Pharm. (2005) 144, 493-501.
Chowdhury, U.R. et al., "Proteome analysis of human aqueous humor," Biochem. Mol. Biol. (2010) 51 (10): 4921-4931.
Chrai, S. S. et al., "Drop size and initial dosing frequency problems of topically applied ophthalmic drugs," J. Pharm. Sci. (1974) 63:333-338.
Ciruela, F. et al., "Immunologicla identification of Al adenosine receptors in brain cortex," J. Neurosci. Res. (1995) 42, 818-828.
Colombe, L. et al., "Prostanoid receptors in anagen human hair follicles," Exp. Derm. (2007) 17:63-72.
Cummings, J. et al., "Enzymology of mitomycin C metabolic activation in tumour tissue: implications for enzyme-directed bioreductive drug development," Biochem. Pharmacol. (1998) 56:405-414.

(56) References Cited

OTHER PUBLICATIONS

Cyr, C. et al., "Prolonged desensitization of the human endothelin A receptor in xenopus oocytes," J. Biol. Chem. (1993) 268, 26071-26074.
Dirks, M. et al., "Efficacy and safety of the ocular hyotensive lipid 192024 in patients with elevated IOP: a 30-day comparison with Latanoprost," Invest. Opthal. Visual Sci. (2000) 41(4):2737-B983.
Draelos, Z.D., "Special considerations in eye cosmetics," Clinics in Dermatology (2001) 19, 424-430.
Easthope, S.E. et al., "Topical bimatoprost: a review of its use in open-angle glaucoma and ocular hypertension," Drugs Aging (2002) 19(3):231-248.
Ernst, O.P. et al., "Mutation of the fourth cytoplasmic loop of Rhodopsin affects binding of transducin and peptides derived from the carboxyl-terminal sequences of transducin α and γ subunits," J. Biol. Chem. (2000) 275, 1937-1943.
Fan, T. et al., "A role for the distal carboxyl tails in generating the novel pharmacology and G protein activation profile of μ and δ opioid receptor hetero-oligomers," J. biol. Chem. (2005) 280, 38478-38488.
FDA Consumer, "New drugs for glaucoma (Lumigan and Travatan)" May 2001, available at http://www.highbeam.com/doc/1G1-75608860.html/print.
FDA Consumer Magazine, "New Drugs for Glaucoma" (May-Jun. 2001) 35(3), 4.
FDA Eye Cosmetic Safety at http://www.fda.gov/cosmetics/productandingredientsafety/productinformation/ucm137241.htm, (Aug. 1, 2001) 2 pages.
Fowler, C.J., "The contribution of cydooxygenase-2 to endocannabinoid metabolism and action," Br. J. Pharmacol. (2007) 152:594-601.
Gandolfi, S.A. et al., "Effect of Bimatoprost on patients with primary open-angle glaucoma or ocular hypertension who are nonresponders to Latanoprost," Ophthal. (2003) 110:609-613.
Garza, L.A. et al., "Prostaglandin 02 inhibits hair growth and is elevated in bald scalp of men with androgenetic alopecia," Sci. Transl. Med. (2012) 4:1-11.
Gaynes, B.I. et al., "Topical ophthalmic NSAIDs: a discussion with focus on Nepfenac ophthalmic suspension," Clin. Ophthal. (2008) 2, 355-368.
Glaucoma Foundation, Treatment update, New drug approved by Food and Drug Administration. Unoprostone isopropyl ophthalmic solution, 15%, Eye to Eye Newsletter, (Fall 2000) 11, p. 10.
Gupta, R. et al., "Evaluating eye drop instillation technique in glaucoma patients," J. Glaucoma (2012) 21:189-192.
Haj-Yehia, A. et al., "Structure-pharmacokinetic rleationships in a series of short fatty acid amides that possess anticonvulsant activity," J. Pharm. Sci. (1990) 79, 719-24.
Hellberg, M.R. et al., "Identification and characteristics of the ocular hypotensive efficacy of Travoprost, a potent and selective prostaglandin receptor agonist and AL-6598, a DP prostaglandin receptor agonist," Surv. Ophthal. (2002) 47:S13-33.
Hirata, T. et al., "Prostanoid receptors," Chem. Rev. (2011) 111(10):6209-6230.
Ho, N.F.H., "Physical model approach to the design of drugs with improved intestinal absorption," in Design of Biopharmaceutical Properties Through Prodrugs and Analogs, Roche ed, (1977) Chapter 8, pp. 136, 177-182.
Hoen, P.A.C. et al., "mRNA degradation controls differentiation state-dependent differences in transcript and splice variant abundance," Nuc. Acids Res. (2010) 39, 556-566.
Honohan, T. et al., "Duration of the activity of the acid, methyl ester and amide of an orally active platelet aggregation inhibitory prostanoid in the rat," Prost. (1980) 19(1):139-153.
Honohan, T. et al., "Hydrolysis of an orally active platelet inhibitory prostanoid amide in the plasma of several species," Prostaglandins (1980) 19(1):123-138.
Hori, H. et al., "The thickness of human scalp: normal and bald," J. Invest. Derm. (1972) 58, 396-399.
Hosoda, M. et al., "Do glaucoma patients use eye drops correctly?" J. Glaucoma (1995) 4:202-206.
Hwang, K. et al., "Thickness of Korean upper eyelid skin at different levels," J. Craniofacial Surgery (2006) 17, 54-56.
Ichhpujani, P. et al., "Comparison of human ocular distribution of dimatoprost and latanoprost," J. Ocular Pharm. Thera. (2012) 28:134-145.
Johnstone, M.A. et al., "Prostaglandin-induced hair growth," Surv. Ophth. (2002) 47(1):S185-202.
Joost, P. et al., "Phylogenetic analysis of 277 human G-protein-coupled receptors as a tool for the prediction of orphan receptor ligands," Genome Biol. (2002) 3(11):0063.1-16.
Kass, M.A. et al., "Madarosis in chronic epinephrine therapy," Arch. Ophthal. (1972) 88:429-431.
Kaupmann, K. et al., "GABA(B)-receptor subtypes assemble into functional heteromeric complexes," Nature (1998) 396, 683-687.
Ke, T-L et al., "Nepafanac, a unique nonsteroidal prodrug with potential utility in the treatment of trauma-induced ocular inflammation," Inflammation (2000) 24, 371-384.
Kelly, C.R et al., "Real-time intracellular Ca2+ mobilization by travoprost acid, bimatoprost, unoprostone an dother analogs via endogenous mouse, rat and cloned human FP prostaglandin receptors," J. Pharm. Exp. Ther. (2003) 304(1):238-245.
Kobilka, B.K. et al., "Chimeric alpha2-, beta2-adrenergic receptors: delineration of domains in volved in effector coupling and ligand binding specificity," Science (1988) 240:1310-1316.
Kolker, A.E., Discussion, Ophthalmology (2001) 108(6):1032.
La Du, B.N., "Pharmacogenetics: defective enzymes in relation to reactions to drugs," Ann. Rev. Med. (1972) 23, 453-468.
Latisse (Bimatoprost Ophthalmic Solution) 0.03% Label (2001).
Lederer, C.M. et al., "Drop size of commercial glaucoma medications," Am. J. Ophthal. (1986) 101:691-694.
Lee, V.H.L. et al., "Improved ocular drugs delivery with prodrugs," in Prodrugs: Topical and Ocular Drug Delivery, Marcel Dekker, New York (1992) 221-297.
Lee, V.H.L. et al., "Review: topical ocular drug delivery: recent developments and future challenges," J. Ocular Pharm. (1986) 2:67-108.
Lumigan (Bimatoprost Opthalmic Solution) 0.03% Package Insert, Mar. 2001.
Maddox, Y.T. et al., "Amide and L-amino derivatives of F prostaglandins as prostaglandin antagonists," Nature (1978) 273:549-552.
Maggio, R. et al., "Reconsitution of functional muscarinic receptors by co-expression of amino- and carboxyl-terminal receptor fragments," Fed. Eur. Biochem. Soc. Lett. (1993) 319, 195-200.
Matias et al., "Prostaglandin ethanolamides (Prostamides): in vitro pharmacology and metabolism," J. Pharm. Exp. Thera. (2004) 309:745-757.
Mentlein, R. et al., "Hydrolysis of ester- and amide-type drugs by purified isoenzymes of nonspecific carboxylesterase from rat liver," Biochem. Pharm. (1984) 33:1243-1248.
Millar, R.P. et al., "Diversity of actions of GnRHs mediated by ligand-induced selective signaling," Frontiers in Neuroendocrinology (2008) 29, 17-35.
Mishima, S. et al., "Determination of tear volume and tear flow," Invest. Ophthal. (1966) 5(3):264-276.
Morris, C.L. et al., "The role of bimatoprost eyelash gel in chemotherapy-induced madarosis: an analysis of efficacy and safety," Int. J. Trichology (2011) 3, 84-91.
NG, G.Y.K., "Phosphorylation and palmitoylation of the human D2L dopamine receptor in Sf9 cells," J. Neurochem. (1994) 63:1589-1595.
Ohashi, P.S. et al., "Reconstitution of an active surface T3/T-cell antigen receptor by DNA transfer," Nature (1985)316:606-609.
Ota, T. et al., "The effects of prostaglandin analogues on IOP in prostanoid FP receptor-deficient mice," Invest. Ophthal. Vis. Sci. (2005) 46, 4159-4163.
Ota, T. et al., The effects of prostaglandin analogues on prostanoid EP1, EP2, and EP3 receptor deficient mice, Invest. Ophthal. Vis. Sci. (2006) 47, 3395-3399.
Ozawa, A. et la., "Deorphanization of novel peptides and their receptors," Am. Assc. Pharm. Sci. (2010) 12(3):378-384.

(56) References Cited

OTHER PUBLICATIONS

Patton, T.F. et al., "Quantitative precorneal disposition of topically applied pilocarpine nitrate in rabbit eyes," J. Pharm. Sci. (1976) 65:1295-1301.
Physician's Desk Reference (2001) Supplement A, "Lumigan" (Mar. 2001) 3 pages.
Pierce, K.L. et al., Cloning of a carboxyl-terminal isoform of the prostanoid FP receptor, J. Biol. Chem. (1997) 272, 883-887.
Pierce, K.L. et al., "Prostanoid receptor heterogeneity through alternative mRNA splicing," Life Sci. (1998) 62:1479-1483.
Pin, J-P. et al., "Alternative splicing generates metabotropic glutamate receptors inducing different patterns of calcium release in xenopus oocytes," Proc. Natl. Acad. Sci. (1992) 89, 10331-10335.
Powell, W.S. et al., "Prostaglandin F2alpha receptor in ovine corpora lutea," Eur. J. Biochem. (1974) 41:103-107.
Ramsey, D. et al., "Homo- and hetero-oligomeric interactions between G-protein-coupled receptors in living cells monitored by two variants of bioluminescence resonance energy transfer (BRET): Hetero-oligomers between receptor subtypes form more efficiently than between less closely related sequences," Biochem. J. (2002) 365:429.
Rath, C.M. et al., "Meta-omic characterization fo the marine invertebrate microbial consortium that produces the chemotherapeutic nature product ET-743," ACS Chem. Biol. (2011) 6, 1244-1256.
Regan, J.W. et al., "Cloning of a novel human prostaglandin receptor with characteristics of the pharmacologically defined EP2 subtype," Mol. Pharm. (1994) 46, 213-220.
Rouzer, C.Z. et al., "Endocannabinoid oxygenation by cyclooxygenases, lipoxygenases, and cytochromes P450: cross-talk between the eicosanoid and endocannabinoid signaling pathways," Chem. Rev. (2011) 111:5899-5921.
Saito, O. et al., "Expression of the prostaglandin F receptor (FP) gene along the mouse genitourinary tract," AJP-Renal Physiol. (2003) 284:F1164-1170.
Salim, K. et al., "Oligomerization of G-protein-coupled receptors shown by selective co-immunoprecipitation," J. Biol. Chem. (2002) 277:15482-15483.
Satoh, T. et al., "The mammalian carboxylesterases: from molecules to functions," Ann. Rev. Pharmacol. & Toxicol. (1998) 38:257-288.
Scarselli, M. et al., "Reconsitution of functional dopamine D2s receptor by co-expression of amino- and carboxyl-terminal receptor fragments," Eur. J. Pharma. (2000) 397, 291-296.
Schaaf, T.K. et al., "Synthesis and biological activity of carboxyl-terminus modified prostaglandin analogues," J. med. Chem. (1979) 22:1340-1346.
Schachtsschabel, U. et al., "The mechanism of action of prostaglandins on oveosclerol outflow," Curr. Op. Ophthal. (2000) 11, 112-115.
Shanbhag, V.r. et al., "Ester and amide prodrugs of ibuprofen and naproxen: synthesis, anti-inflammatory activity, and gastrointestinal toxicity," J. Pharm. Sci. (1992) 81, 149-154.
Sharif, N.A. et al., "Agonist activity of Bimatoprost, Tavoprost, Latanoprost, Unoprosone, Isopropyl Ester and other prostaglandin analogs at the cloned human ciliary body FP prostaglandin receptor," J. ocular Pharmacol. Therap. (2002) 18, 313-324.
Sharif, N.A. et al., "Bimatoprost (Lumigan) is an agonist at the cloned human ocular FP prostaglandin receptor: real-time FLIPR-based intracellular Ca2+ mobilization studies," Prostaglandin Leukotrienes & Essential Fatty Acids (2003) 68:27-33.
Sheerer, P. et al., "Crystal structure of opsin in its G-protein-interacting conformation," Nature (2008) 455, 497-502.
Shell, J.W., "Ophthalmic drug delivery systems," Survey Ophthal. (1984) 29(2):117-128.
Shell, J.W., "Pharmacokinetics of topically applied ophthalmic drugs," Surv. Ophthal. (1982) 26(4):207-218.
Singer, I.I. et al., "CCR5, CXCR4, and CD4 are clustered and closely apposed on microvilli of human macrophages and T cells," J. Virol. (2001) 75(8):3779-3790.
Sorbera, L.A. et al., "Travoprost" Drugs of the Future (2000) 25(1):41-45.
Stern, F.A. et al., "Comparison of the hypotensive and other ocular effects of prostaglandins E2 and F2 alpha on cat and rhesus monkey eyes," Invest. Ophthal & Vis. Sci. (1982) 22, 588-598.
Stjernschantz et al., "Preclinical pharmacology of Latanoprost, a phenyl-substituted PGF2alpha analogue," Adv. Prostagldin Thromboxane & Leukotriene Res. (1995) 23:513-518.
Stulting, R.D. et al., "Diagnosis and management of tear film dysfunction," in Corneal Disorders; Clinical Diagnosis and Management (Leibowitz et al. eds) (1998) Chapter 16, 482-500.
Svensson, et al., "The design and bioactivation of presystemically stable prodrugs," Drug Metabolism Rev. (1988) 19(2):165-194.
Tauchi, M. et al., "Characterization of an in vivo model for the study of eyelash biology and trichomegaly: mouse eyelash morphology, development, growth cycle and anagen prolongation by bimatoprost," Br. J. Derm. (2010) 162, 1186-1197.
Thomas, W. et al., "Stable expression of a truncated AT1A receptor in CHO-K1 cells," J. Biol. Chem. (1995) 270:207-213.
Tomasz, M., "Mitomycin C: small, fast and deadly (but very selective)," Chem. Biol. (1995) 2, 575-579.
Toris, C.B. et al., "Update on the mechanism of action of topical prostaglandins for intraocular pressure reduction," Surv. Ophthal. (2008) 53, S107-S120.
Travatan (Travoprost Opthalmic Solution) 0.04% Product Insert (Published Mar. 16, 2001), 7 pages.
Trinkaus-Randall, V. et al., "Corneal structure and function," in Corneal Disorders: Clinical Diagnosis and Management, Howard M. Leibowitz et al. eds., (1998) 2nd Edition, p. 2-31.
Trueb, R.M., "Chemotherapy—induced alopecia," Seminars Cutaneous Med. & Surg. (2009) 28, 11-14.
Ungrin, M.D. et al., "Key structural features of prostaglandin E2 and prostanoid analogs involved in binding and activation of the human EP1 prostanoid receptor," Mol. Pharm. (2001) 59, 1446-1456.
Van Santvliet, L. et al., "Determinants of eye drop size," Surv. Ophthal. (2004) 49(2):197-213.
Vandenburgh, A.M., reply to Alan L. Robin, "An accurate comparison of Bimatoprost's efficacy and adverse effects," Arch. Ophthal. (2002) 120:1000.
Vassilatis, D. et al., "The G protein-coupled receptor repertoires of human and mouse," Proc. Natl. Acad. Sci. USA (2003) 100, 4903-4908.
Walsh, D.A. et al., "Anti-inflammatory agents, syntheses and biological evaluation of potential prodrugs of 2-amino-3-benzoylbenzeneacetic acid and 2-amino-3-(4-chlorobenzoyl)benzeneacetic acid," J. Med. Chem. (1990) 33, 2296-2304.
Wan, Z. et al., "Bimatoprost, prostamide activity, and conventional drainage," Invest. Ophthal. Vis. Sci. (2007) 48, 4107-4115.
Warne, T. et al., "Expression and purification of truncated, non-glycosylated Turkey beta-adrenergic receptors for crystallization," Biochimica et Biophysica Acta—Biomembranes (2003) 1610, 133-140.
Warne, T. et al., "Structure of a beta1-adrenergic G-protein-coupled receptor," Nature (2008) 454:486-491.
Weber, A. et al., "Formation of prostamides from anandamide in FAAH knockout mice analyzed by HPLC with tandem mass spectrometry," J. Lipid Res. (2004) 45, 757-763.
Whitson, J.T., "Travoprost—a new prostaglandin analogue for the treatment of glaucoma," Exp. Op. Pharmacotherapy (2002) 3(7):965-977.
Winfield, A.J. et al., "A study of the causes of non-compliance by patients prescribed eyedrops," Br. J. Ophthal. (1990) 74:477-480.
Witkowski, A. et al., "Head-to-head coiled arrangement of the subunits of the animal fatty acid synthase," Chem. Biol. (2004) 11, 1667-1676.
Woodward, D.F. et al., "Prostaglandins F2alpha (PGF2alpha) 1-ethanolamide: a pharmacologically unique local hormone biosynthesized from anandamide," 11th Int. Conf. Advances Prostaglandin & Leukotrine Res: Basic Sci and New Clinical Applications—abstract book (2000) 27.

(56) References Cited

OTHER PUBLICATIONS

Xalatan (Latanoprost Opthalmic Solution) 0.005% product insert (Published Jun. 6, 2001), 5 pages.

Yang, W. et al., "Enzymatic formation of prostamide F2alpha from anandamide involves a newly identified intermediate metabolite, prostamide H2," J. Lipid Res. (2005) 46, 2745-2751.

Yuan, X. et al., "Quantitative proteomics: comparison of the macular bruch membrane/choroid complex from age-related macular degeneration and normal eyes," Mol. Cell Proteomics (2010) 9:1031-1046.

Zioptan (Tafluprost Opthalmic Solution) 0.0015% product insert (Published Feb. 10, 2012), 12 pages.

United States Patent Office Final Rejection for U.S. Appl. No. 12/260,534 dated Apr. 23, 2012 (10 pages).

Higginbotham, E.J. et al., "One-year randomized study comparing bimatoprost and timololin in glaucoma and ocular hypertension," Arch. Ophthal. (2002) 120(10):1286-1293.

United States Patent Office Action for U.S. Appl. No. 12/479,532 dated May 10, 2011 (5 pages).

* cited by examiner

AMINO ACID SALTS OF PROSTAGLANDINS

TECHNICAL FIELD

The present invention is directed to novel amino acid salts of prostaglandins and methods of making and using the same.

BACKGROUND OF THE INVENTION

Various prostaglandins are useful for the treatment of medical conditions including, for example: ocular disorders, such as glaucoma; skin disorders; circulatory disorders, such as hypertension; gastrointestinal disorders; hair loss; respiratory disorders; fertility control; and bone disorders, such as osteoporosis. Information regarding the biological effects of Prostaglandin F analogs is disclosed in the following references: PCT Publication No. WO 99/12895, 1999; PCT Publication No. WO 99/12896, 1999; PCT Publication No. WO 99/12898; Abstr. 1999, 194116 "Molecular mechanisms of diverse actions of prostanoid receptors", *Biochimica et Biophysica Acta,* 1259 (1995) 109-120; U.S. Pat. No. 3,776,938 issued to Bergstrom, S., and Sjovall, J., Dec. 4, 1973; U.S. Pat. No. 3,882,241 issued to Pharriss, G., May 6, 1975; G.B. Patent No. 1,456,512 (1976) issued to Pfizer Inc., Bundy, G. L.; Lincoln, F. H., "Synthesis of 17-Phenyl-18,19,20-trinor prostaglandins I. The PG1 Series", *Prostaglandins* Vol. 9 (1975) pp. 1-4; CRC Handbook of Eicosanoids: Prostaglandins and Related Lipids Vol. 1, Chemical and Biochemical Aspects, Parts A & B, A. L. Willis, eds., CRC Press (1987); Liljebris, C.; et. al. "Derivatives of 17-Phenyl-18,19,20-trinorprostaglandin F2α Isopropyl Ester Potential Antiglaucoma Agents", *Journal of Medicinal Chemistry* Vol. 38, (1995), pp. 289-304; Collins, P. W.; Djuric, S. W. "Synthesis of Therapeutically Useful Prostaglandin and Prostacyclin Analogs", *Chemical Reviews* 93 (1993), pp. 1533-1564.

All naturally occurring prostaglandins, including $PGF_{2\alpha}$, and almost all non-naturally-occurring prostaglandins possess a carboxylic acid moiety at the $C_1$ position. The carboxylic acid moiety is a site for metabolic degradation by beta oxidation, which contributes to the rapid metabolism of the naturally occurring prostaglandins. Attempts to prevent beta oxidation by modifying the carboxylic acid moiety at the 1 position as an ester moiety, a sulfonamide moiety, and as a tetrazole are known in the art (See e.g. PCT Publication No. WO 99/12895, 1999; PCT Publication No. WO 99/12896, 1999; PCT Publication No. WO 99/12898). However, such modifications have either resulted in only modest increases in half-life (such as the esters) or resulted in compounds with diminished potency.

Prostaglandin F analogs wherein $C_1$ itself is replaced with a heteroatom have also been described in the art. For example, PGF analogs containing a sulfonic acid moiety at $C_1$ (The chemistry of prostaglandins containing the sulfo group. Iguchi, Y.; Kori, S.; Hayashi, M. *J. Org. Chem.,* 40, pp. 521-523 1975) and PGF analogs containing a phosphonic acid moiety at $C_1$ (The Synthesis of dimethylphosphonoprostaglandin analogs, Kluender, H. C. & Woessner, W. *Prostaglandins and Medicine,* 2: pp. 441-444, 1979) have been disclosed. However, such compounds suffer from significantly diminished potency. However, the potent $C_1$ carboxylic acids are difficult to purify as they are most often synthesized as oils. There is a need for solid forms of prostaglandins, both naturally and non-naturally occurring, for the purposes of purification and as intermediates in synthesis, as well as the direct use of these solids in drug products.

SUMMARY OF THE INVENTION

The present invention provides an amino acid salt of a prostaglandin free acid. In another embodiment, the present invention provides a pharmaceutical composition including the amino acid salt of a prostaglandin free acid and a pharmaceutically acceptable carrier. The present invention also provides methods of making the salt comprising reacting an amino acid with a prostaglandin free acid.

Further, the invention provides methods of making a prostaglandin analog from the amino acid salt of a prostaglandin free acid. In addition, the invention provides methods of making prostaglandins from the salts.

The present invention also provides methods of treating eye diseases, such as glaucoma, treating bone disorders, such as osteoporosis, treating skin disorders, treating respiratory disorders, treating circulatory disorders such as hypertension, treating gastrointestinal disorders, treating hair loss, fertility control, improving nasal patency or treating neurogenic bladder comprising administering an amino acid salt of a prostaglandin free acid. In addition, the present invention provides method of reducing ocular pressure comprising contacting a cell with an amount of the salt effective to reduce ocular pressure.

DETAILED DESCRIPTION OF THE INVENTION

The present invention is directed to novel amino acid salts of prostaglandin free acids and methods of making and using the amino acid prostaglandin salts of the present invention. The amino acid prostaglandin salts are useful in methods of treating eye diseases, such as glaucoma. The amino acid prostaglandin salts of the present invention are also useful in a method of treating bone disorders, such as osteoporosis, treating skin disorders, treating respiratory disorders, treating circulatory disorders such as hypertension, treating gastrointestinal disorders, treating hair loss, fertility control, improving nasal patency or treating neurogenic bladder. Further, the amino acid prostaglandin salts of the present invention are useful for purifying prostaglandins and prostaglandin intermediates and as intermediates in the production of both protected and unprotected prostaglandin analogs.

Definitions And Usage Of Terms

"Alcohol protecting group" refers to a protecting group that replaces the active hydrogen of a hydroxyl moiety thus preventing undesired side reaction at the hydroxyl moiety. Use of alcohol protecting groups in organic synthesis is well known in the art. Examples of alcohol protecting groups are found in Chapter 2 of Theodora W. Greene's text entitled: "Protective Groups in Organic Synthesis" ($3^{rd}$ Edition). Suitable alcohol protecting groups include silyl ethers, alkoxymethyl ethers, tetrahydropyranyl, tetrahydrofuranyl, esters, and substituted or unsubstituted benzyl ethers. If more than one alcohol protecting group is present, the alcohol protecting groups may be the same or different. In some embodiments, the alcohol protecting groups may be orthogonal.

"Alkyl" refers to a saturated or unsaturated hydrocarbon chain having 1 to 18 carbon atoms, suitably 1 to 12 carbon atoms, or 1 to 6 carbon atoms, or 1 to 4 carbon atoms. Alkyl groups may be straight or branched. In some embodiments, branched alkyl groups have one or two branches. Unsaturated alkyl groups have one or more double bonds and/or one or more triple bonds. Suitably, unsaturated alkyl groups have one or two double bonds or one triple bond. Alkyl chains may be unsubstituted or substituted with from 1 to about 4 substituents unless otherwise specified. Suitably, alkyl groups are mono-, di-, or tri-substituted. Suitable alkyl substituents include, but are not limited to, cyano, halo, hydroxy, aryl (e.g., phenyl, tolyl, alkyloxphenyl, alkyloxycarbonylphenyl, halophenyl), heterocyclyl, and heteroaryl.

"Aromatic ring" refers to an aromatic hydrocarbon ring system. Aromatic rings are monocyclic or fused bicyclic ring systems. Monocyclic aromatic rings contain from about 5 to about 10 carbon atoms, suitably from 5 to 7 carbon atoms, or from 5 to 6 carbon atoms in the ring. Bicyclic aromatic rings contain from 8 to 12 carbon atoms, suitably 9 or 10 carbon atoms in the ring. Aromatic rings may be unsubstituted or substituted with from 1 to about 4 substituents on the ring. Suitable aromatic ring substituents include, but are not limited to, halo, cyano, lower alkyl, heteroalkyl, haloalkyl, phenyl, phenoxy or any combination thereof. Suitably, the aromatic ring substituents are lower alkyl, cyano, halo or halo alkyl.

"Basic amino acid" refers to naturally-occurring and non-naturally-occurring alpha, beta and gamma amino acids, including all enantiomers and diastereomers, whether protected or unprotected, provided that the amino acids have a net positive charge at neutral pH. Neutral pH is a pH from about 6.5 to about 7.5. The basic amino acid may be basic when it is the free acid form, or it may only be basic as the ester or amide form of the amino acid. Suitable basic amino acids that are basic in the free acid form include, but are not limited to, arginine, lysine, histidine, L-Arginine, D-Arginine, DL-Arginine, homoarginine, 3- and 4-substituted arginine analogs, N(delta)-methyl-L-arginine (deltaMA), L-canavanine, D-canavanine, DL-canavanine, protected and/or substituted analogs of canavanine, L-α-Amino-β-guanidinopropionic acid, γ-guanidinobutyric acid, citrulline, 3-guanidinopropionic acid, 4-{[amino(imino)methyl]amino}butanoic acid, 6-{[amino(imino)methyl]amino}hexanoic acid, L-2-Amino-3-guanidinopropionic acid, L-Homoarginine, L-Arginine hydroxamate, Agmatine (CAS #: 2482-00-0), and NG-Methyl-L-arginine (CAS #: 53308-83-1). Other amino acids can be made into a basic amino acid if the acid group or groups are suitably protected. Suitable examples of basic amino acids that are esters include L-Arginine ethyl ester. Suitable examples of basic amino acids that are protected as amides include, but are not limited to, L-Argininamide, L-Arginine N-ethylamide, and Arg-beta-Ala hydrochloride, (CAS #: 98957-79-0). In some embodiments, the basic amino acid comprises a guanidino group.

"Carbocycle" refers to a saturated or unsaturated hydrocarbon ring. Carbocycles are not aromatic. Carbocycles are monocyclic, or are fused, spiro, or bridged bicyclic ring systems. Monocyclic carbocycles contain from about 4 to about 10 carbon atoms, suitably from 4 to 7 carbon atoms, or from 5 to 6 carbon atoms in the ring. Bicyclic carbocycles contain from 8 to 12 carbon atoms, suitably from 9 to 10 carbon atoms in the ring. Carbocycles may be unsubstituted or substituted with from 1 to about 4 substituents on the ring. Suitable carbocycle substituents include, but are not limited to, halo, cyano, lower alkyl, heteroalkyl, haloalkyl, phenyl, phenoxy or any combination thereof. Suitably, the carbocycle substituents are halo or haloalkyl. Suitable carbocycles include, but are not limited to, cyclopentyl, cyclohexyl, cyclohexenyl, cycloheptyl, and cyclooctyl.

"Halo" refers to fluoro, chloro, bromo or iodo.

"Haloalkyl" refers to a straight, branched, or cyclic hydrocarbon substituted with one or more halo substituents. Suitably, the haloalkyl is $C_1$-$C_{12}$, or $C_1$-$C_6$ or $C_1$-$C_3$. Suitable halo substituents include fluoro and chloro. One suitable haloalkyl is trifluoromethyl.

"Heteroalkyl" refers to a saturated or unsaturated chain containing carbon and at least one heteroatom, wherein no two heteroatoms are adjacent. Heteroalkyl groups contain from 1 to 18 member atoms (carbon and heteroatoms) in the chain, or 1 to 12 member atoms, or 1 to 6 member atoms, or 1 to 4 member atoms. Heteroalkyl groups may be straight or branched. Suitably, the branched heteroalkyl may have one or two branches. Unsaturated heteroalkyl have one or more double bonds and/or one or more triple bonds. Suitably, heteroalkyl groups have one or two double bonds or one triple bond. Heteroalkyl groups may be unsubstituted or substituted with from 1 to about 4 substituents unless otherwise specified. Suitable heteroalkyl substituents include halo, aryl (e.g., phenyl, tolyl, alkyloxyphenyl, alkyloxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), amino (e.g., amino, mono- and di-$C_1$-$C_3$ alkanylamino, methylphenylamino, methylbenzylamino, $C_1$-$C_3$ alkanylamido, carbamamido, ureido, guanidino).

"Heteroatom" refers to a nitrogen, sulfur, or oxygen atom. Groups containing more than one heteroatom may contain different heteroatoms. As used herein, halogens are not heteroatoms.

"Heterocycle" refers to a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocycles are not aromatic. Heterocycles are monocyclic, or are fused or bridged bicyclic ring systems. Monocyclic heterocycles contain from about 4 to about 10 member atoms (carbon and heteroatoms), suitably from 4 to 7 member atoms, or from 5 to 6 member atoms in the ring. Bicyclic heterocycles contain from 8 to 12 member atoms, suitably 9 or 10 member atoms in the ring. Heterocycles may be unsubstituted or substituted with from 1 to about 4 substituents on the ring. Suitably, the substituents are halo or haloalkyl. Suitable heterocycle substituents include: halo, cyano, lower alkyl, heteroalkyl, haloalkyl, phenyl, phenoxy or any combination thereof. Suitable heterocycles include, but are not limited to, piperzyl, morpholinyl, tetrahydrofuranyl, tetrahydropyranyl and piperdyl.

"Heteroaryl" refers to an aromatic ring system containing carbon and from 1 to about 4 heteroatoms in the ring. Heteroaryls are monocyclic or fused bicyclic ring systems. Monocyclic heteroaryls contain from about 5 to about 10 member atoms (carbon and heteroatoms), or from 5 to 7 member atoms, or from 5 to 6 member atoms in the ring. Bicyclic heteroaryls contain from 8 to 12 member atoms, or 9 or 10 member atoms in the ring. Heteroaryls may be unsubstituted or substituted with from 1 to about 4 substituents on the ring. Suitable heteroaryl substituents include: halo, cyano, lower alkyl, heteroalkyl, haloalkyl, phenyl, phenoxy or any combination thereof. Suitably, the substituents are halo, haloalkyl or phenyl. Suitable heteroaryls include, but are not limited to, benzothienyl, benzofuranyl, thienyl, thiazolo, purinyl, pyrimidyl, pyridyl, and furanyl.

"Lower alkyl" refers to an alkyl chain comprised of 1 to 4 carbon atoms, suitably 1 to 3 carbon atoms or 1 to 2 carbon atoms. Lower alkyl groups may be saturated or unsaturated and substituted or unsubstituted. Lower alkyl groups include, but are not limited to, methyl, ethyl, propyl, isopropyl, butyl, isobutyl and t-butyl.

"Lower heteroalkyl" refers to a heteroalkyl chain comprised of 1 to 4 member atoms. Lower heteroalkyl groups may be saturated or unsaturated and substituted or unsubstituted.

"Member atom" refers to a polyvalent atom (C, O, N, or S atom) in a chain or ring system that continues the chain or ring system. For example, in benzene the six carbon atoms are member atoms and the six hydrogen atoms are not member atoms.

"Phenyl" refers to a six-membered monocyclic aromatic ring which may or may not be substituted with from about 1 to about 4 substituents. The substituents may be substituted at the ortho, meta or para position on the phenyl ring, or any combination thereof. Suitable phenyl substituents include: halo, cyano, lower alkyl, heteroalkyl, haloalkyl, phenyl, phenoxy or any combination thereof.

"Prostaglandin analog" refers to a compound that is designed to bind to a prostaglandin receptor. Prostaglandin analogs include protected prostaglandins, e.g. prostaglandins with esters or amides at the C1 position.

"Prostaglandin free acid" refers to a prostaglandin, prostaglandin analog or prostaglandin intermediate that has a carboxylic acid moiety at the C1 position.

"Prostaglandin intermediate" refers to a compound that is on the synthetic pathway to a compound that, in its active form, stimulates one or more of the prostaglandin receptors. Prostaglandin intermediates may be a protected prostaglandin or prostaglandin analog or they may have parts of their structures not yet attached. An example of a prostaglandin intermediate is a latanoprost free acid containing one or more silyl protecting groups on an alcohol moiety.

"Prostaglandin F analog" or "PGF analog" or "analog of $PGF_{2\alpha}$," refers to a compound that is structurally similar to naturally occurring $PGF_{2\alpha}$.

"Prostaglandin E analog" or "PGE analog" or "analog of $PGE_2$" or "analog of $PGE_1$" refers to a compound that is structurally similar to naturally occurring $PGE_2$.

"Prostaglandin D analog" or "PGD analog" or "analog of $PGD_2$" refers to a compound that is structurally similar to naturally occurring $PGD_2$.

"Protected" refers to a chemical structure wherein one or more of the chemically-sensitive groups in the molecule have been modified to reduce its activity and allow for better synthetic techniques to be used. In prostaglandins, typical groups where protection is used are the hydroxy groups and the carboxcyclic acid group. Less commonly protected are the ketones found in PGD and PGE analogues. Protecting groups vary but are generally found in "Protecting Groups in Organic Synthesis" by Theadora Green.

"Unprotected" refers to a chemical structure that does not contain any groups that have been added to protect sensitive functional moieties such as hydroxy groups or carboxcyclic acid groups.

"Pharmaceutically acceptable carrier" refers to a carrier that is useful for the preparation of a pharmaceutical composition that is: generally compatible with the other ingredients of the composition, not deleterious to the recipient, and neither biologically nor otherwise undesirable.

"A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" refers to a physiologically compatible additives useful in preparation of a pharmaceutical composition. Examples of pharmaceutically acceptable carriers and excipients can for example be found in Remington Pharmaceutical Science, 16th Ed.

"Therapeutically effective amount" refers to a dosage of the compounds or compositions effective for influencing, increasing, decreasing the activity of a receptor, in particular a prostaglandin receptor in a mammal. This term as used herein may also refer to an amount effective at bringing about a desired in vivo effect in a mammal, preferably, a human, such as reduction in intraocular pressure.

"Administering" refers to administration of the compounds as needed to achieve the desired effect.

"Eye disease" includes, but is not limited to, glaucoma, allergy, cancers of the eye, neurodegenerative diseases of the eye, and dry eye.

The term "contacting a cell" is used to mean contacting a cell in vitro or in vivo (i.e. within a subject, such as a mammal, including humans, rabbits, cats and dogs).

Amino Acid Prostaglandin Salts

The present invention is directed to novel amino acid salts of prostaglandin free acids. Suitable salts include those of Formula I below:

$$[A]^-[\text{Amino Acid}]^+$$

wherein $[A]^-$ is an anion of a prostaglandin free acid. The invention also includes all optical isomers, diastereomers and enantiomers of the above salts. In one embodiment, the stereochemistry at all stereocenters is that of the naturally-occurring amino acid and naturally-occurring prostaglandin.

In some embodiments, the amino acid is a basic amino acid.

In some embodiments, the amino acid prostaglandin salts according to the present invention comprise a prostaglandin free acid of Formula II shown below:

II

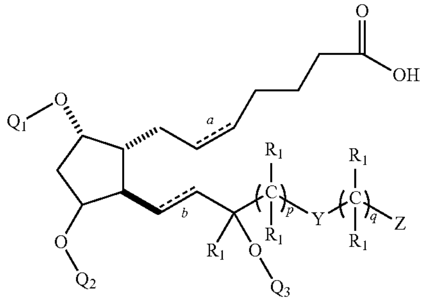

or optical isomers, diastereomers, or enantiomers thereof;

wherein a and b are, independently, single, double or triple bonds;

wherein $Q_1$, $Q_2$, and $Q_3$ are independently selected from hydrogen or an alcohol protecting group;

wherein each $R_1$ is, independently selected from hydrogen or lower alkyl;

wherein Y is —O—, —S—, —S(O), —$SO_2$—, —$C(R^2)_2$—, —$NR^1$—, —$CR^2$=$CR^2$—, or —C≡C—;

wherein Z is selected from hydrogen, carbocycle, aryl or heteroaryl;

wherein each $R^2$, if present, is independently selected from hydrogen, lower alkyl, alkoxy, or hydroxyl; and wherein p, and q are independently an integer of from 0 to 4.

Suitably, no carbon atom in Formula II has two or more heteroatoms attached to it unless the two or more heteroatoms are member atoms in a heteroaromatic ring system.

In Formula II above, the relative stereochemistry at $C_8$, $C_9$, and $C_{12}$ is as specified above. That is, the bond between $C_7$ and $C_8$ is in the α orientation, the alcohol (protected or unprotected) at $C_9$ is in the α orientation, and the bond between $C_{12}$ and $C_{13}$ is in the β orientation. The invention also includes optical isomers, diastereomers and enantiomers of the above structure. At all stereocenters where stereochemistry is not defined (e.g. $C_{11}$ and $C_{15}$), both epimers are envisioned. In some embodiments of the present invention, stereochemistry at all such stereocenters of the invention mimic that of naturally occurring $PGF_{2\alpha}$.

In some embodiments, $Q_1$ is either H or an alcohol protecting group and $Q_2$ and $Q_3$ are alcohol protecting groups. In other embodiments, $Q_1$, $Q_2$, and $Q_3$ are all alcohol protecting groups and may be different alcohol protecting groups and may be the same alcohol protecting group.

Suitable prostaglandin free acids include bimatoprost free acid, fluprostenol free acid, latanoprost free acid, tafluprost free acid and travoprost free acid.

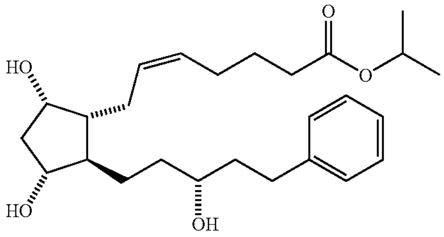

latanoprost

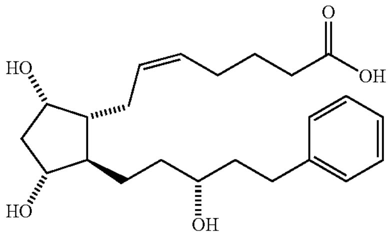

latanoprost free acid

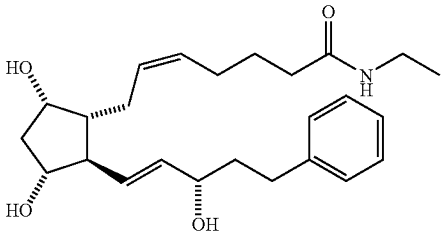

bimatoprost

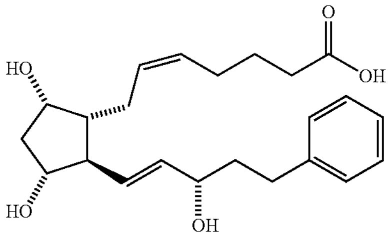

bimatoprost free acid

-continued

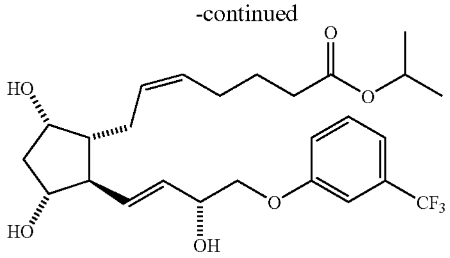

travoprost

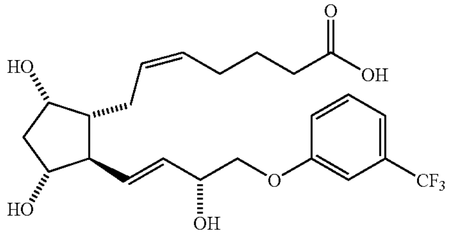

travoprost free acid

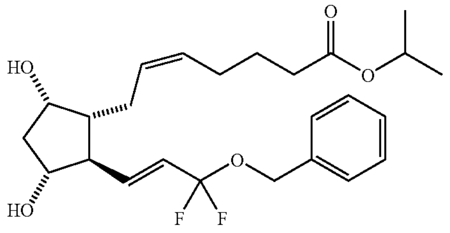

tafluprost

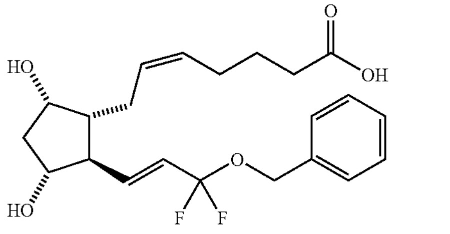

tafluprost free acid

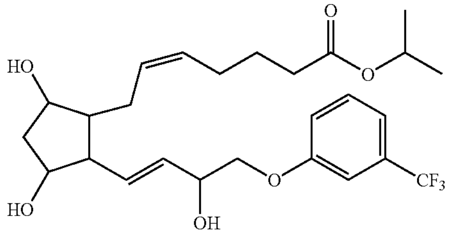

fluprostenol

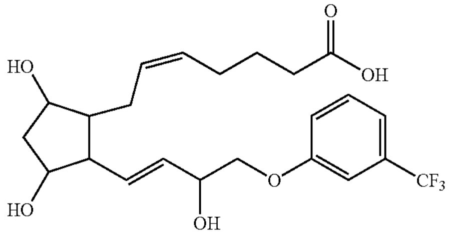

fluprostenol free acid

The amino acid prostaglandin salts of the present invention are readily formulatable and recrystallizable. They generally are dry free-flowing powders with relatively low tackiness and thus are useful in manufacture. Suitably, the salts have a melting point of at least about 35° C. or at least about 50° C.

Amino acid prostaglandin salts according to the present invention include, but are not limited to, those shown below:

7-((1R,2R,3R,5S)-3,5-dihydroxy-2-((S,E)-3-hydroxy-5-phenylpent-1-enyl)cyclopentyl)heptanoic acid, arginine salt:

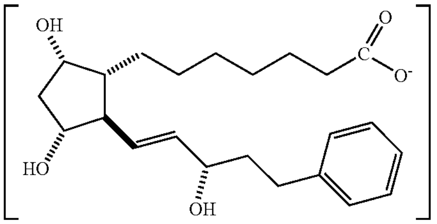

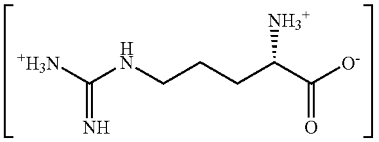

7-((1R,2R,3R,5S)-3,5-dihydroxy-2-((R)-3-hydroxy-4-phenoxybutyl)cyclopentyl)heptanoate, arginine salt:

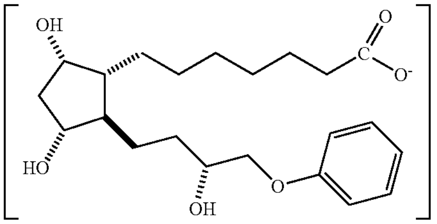

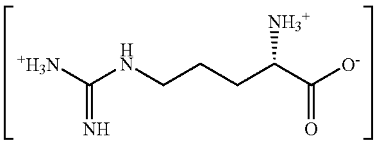

Arginyl (Z)-7-((1R,2R,3R,5S)-3,5-dihydroxy-2-((R,E)-3-hydroxy-4-phenoxybut-1-enyl)cyclopentyl)hept-5-enoate:

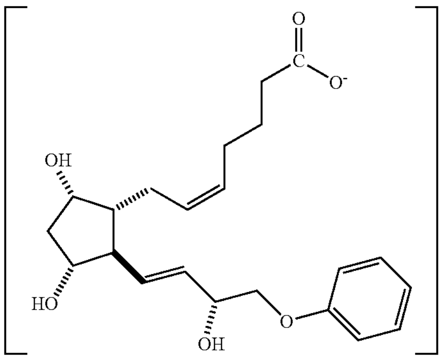

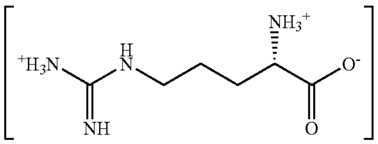

Arginyl (Z)-7-((1R,2R,3R,5S)-2-((R,E)-4-(3-chlorophenoxy)-3-hydroxybut-1-enyl)-3,5-dihydroxy cyclopentyl)hept-5-enoate:

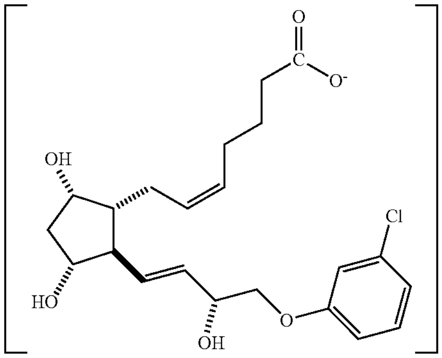

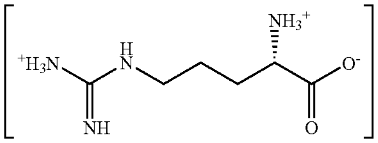

Arginyl (Z)-7-((1R,2R,3R,5S)-3,5-dihydroxy-2-((R,E)-3-hydroxy-4-(3-(trifluoromethyl)phenoxy) but-1-enyl)cyclopentyl)hept-5-enoate
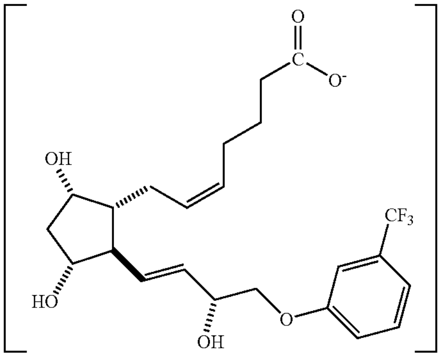
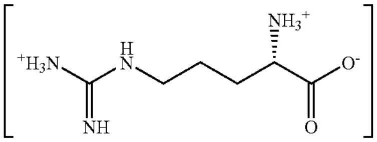
Arginyl (Z)-7-((1R,2R,3R,5S)-2-((R,E)-4-(2-fluorophenoxy)-3-hydroxybut-1-enyl)-3,5-dihydroxycyclopentyl)hept-5-enoate
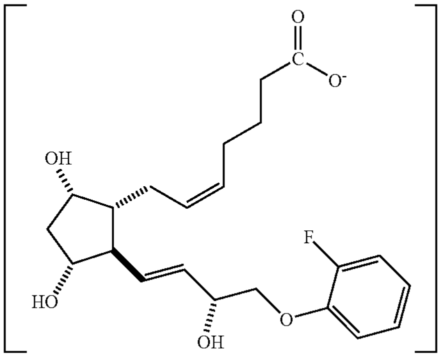
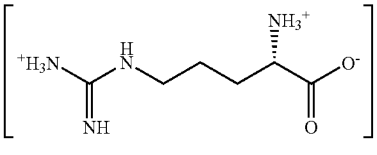
Arginyl (Z)-7-((1R,2R,3R,5S)-2-((R,E)-4-(2-fluorophenylthio)-3-hydroxybut-1-enyl)-3,5-dihydroxycyclopentyl)hept-5-enoate
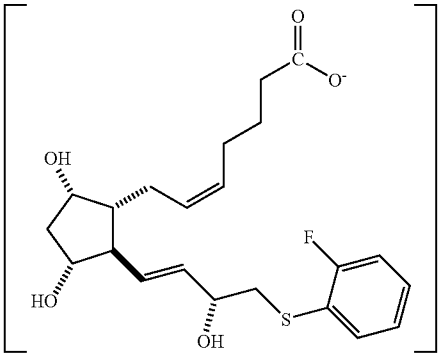
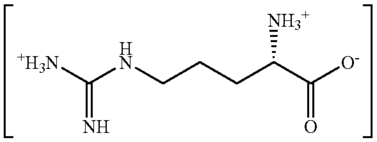
Arginyl 7-((1R,2R,3R,5S)-2-((R)-5-(2-fluorophenyl)-3-hydroxypent-4-ynyl)-3,5-dihydroxycyclopentyl)heptanoate
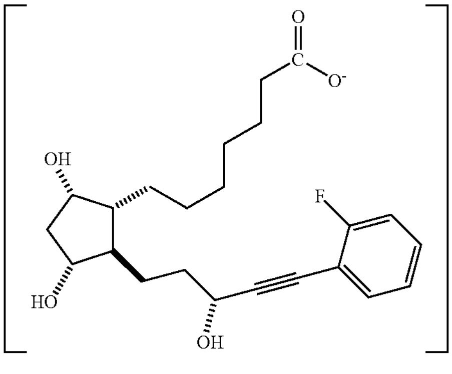
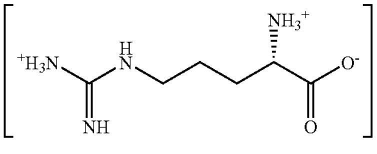

Arginyl 7-((1R,2R,3R,5S)-2-((R)-4-(2-fluorophenylthio)-3-hydroxybutyl)-3,5-dihydroxy cyclopentyl) heptanoate
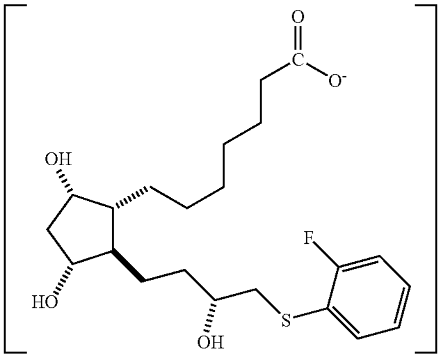
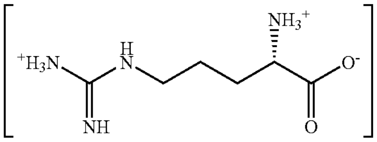
Arginyl (Z)-7-((1R,2R,3R)-3-hydroxy-2-((S,E)-3-hydroxy-5-phenylpent-1-enyl)-5-oxo cyclopentyl) hept-5-enoate
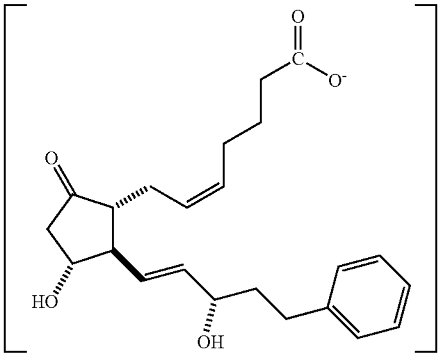
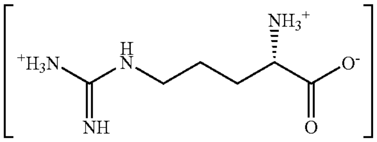
Arginyl 7-((1R,2R,3R)-3-hydroxy-2-((S,E)-3-hydroxy-5-phenylpent-1-enyl)-5-oxocyclopentyl)heptanoate
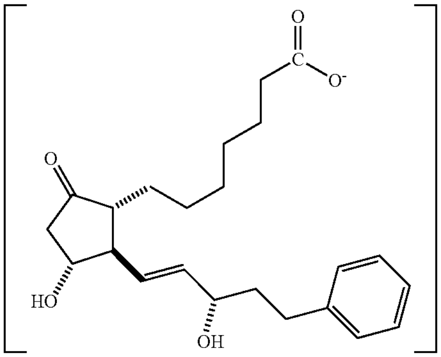
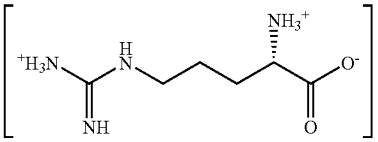
$PGE_1$, arginine salt
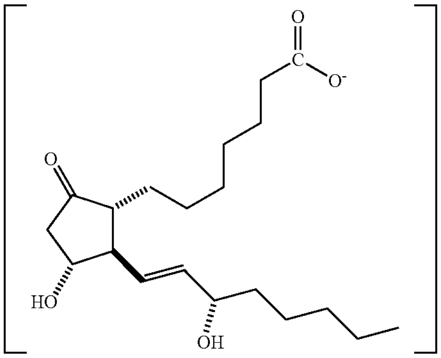
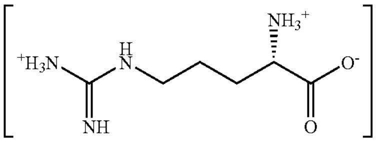

$PGE_2$, arginine salt

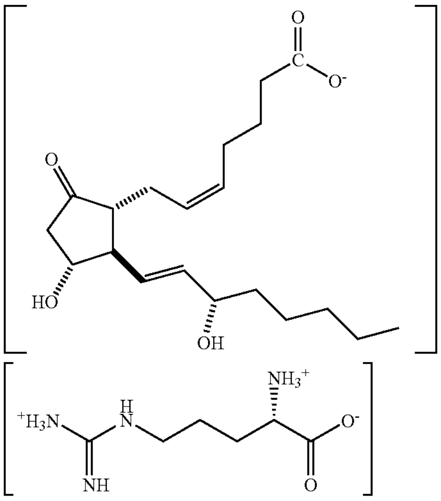

PGD2 arginine salt:

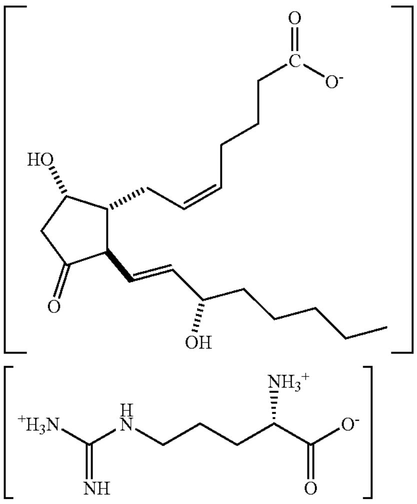

Other prostaglandins and related compounds suitable for use in the present invention include, but are not limited to, those found in the following US and World Patents and patent applications, which are incorporated herein by reference.

1. 5-Thia-omega substituted phenyl-prostaglandin E derivatives, process for producing the same and drugs containing the same as the active ingredient. WO 00/3980.

2. Aromatic $C_{16}$-$C_{20}$-substituted tetrahydro prostaglandins useful as FP agonists WO 99/12895; U.S. Pat. No. 5,977,173, Nov. 2, 1999.

3. Aromatic C16-C20-substituted tetrahydro prostaglandins useful as FP agonists WO 99/12898.

4. Aromatic C16-C20-substituted tetrahydro prostaglandins useful as FP agonists. WO 99/12896, U.S. Pat. No. 6,048,895 Apr. 11, 2000.

5. Prostaglandins of the F series U.S. Pat. No. 5,770,759. Jun. 23, 1998.

6. $EP_2$-receptor agonists as neuroprotective agents for the eye WO 99/26629.

7. Prostaglandin derivatives for the treatment of glaucoma or ocular hypertension. U.S. Pat. No. 6,030,999, Feb. 29, 2000.

8. Cyclopentane heptan(ene)oic acid, 2-heteroarylalkenyl derivatives as therapeutic agents WO 99/25358; U.S. Pat. No. 6,037,364 Mar. 14, 2000.

9. Use of cloprostenol and fluprostenol analogues to treat glaucoma and ocular hypertension U.S. Pat. No. 5,889,052, Mar. 30, 1999.

10. Cis-delta-4-analogs of prostaglandins as ocular hypotensives. WO 98/21182; U.S. Pat. No. 5,994,397 Nov. 30, 1999.

11. Tetrahydrofuran analogs of prostaglandins as ocular hypotensives. WO 98/57930; U.S. Pat. No. 6,025,392 Mar. 14, 2000.

12. Conformationally rigid aryl- or heteroaryl prostaglandins for use in glaucoma therapy. WO 98/21180.

13. Ostaglandins as ocular hypotensives WO 98/57930.

14. Keto-substituted tetrahydrofuran analogs of prostaglandins as ocular hypotensives WO 98/57930.

15. 13-oxa prostaglandins for the treatment of glaucoma and ocular hypertension WO 99/32441.

16. 13-Thia prostaglandins for use in glaucoma therapy WO 98/39293.

17. 162. Alcon Laboratories, Inc. (Sallee V L, Hellberg M R, Klimko P G) 15-Ketal prostaglandins for the treatment of glaucoma or ocular hypertension WO 98/20881.

18. 9-Oxa prostaglandin analogs as ocular hypotensives. WO 98/57942.

19. 15-Fluoro prostaglandins as ocular hypotensives WO 98/21181.

20. 11-Halo prostaglandins for the treatment of glaucoma or ocular hypertension WO 98/20880.

21. Use of 9-deoxy prostaglandin derivatives to treat glaucoma WO 96/10407.

22. Prostaglandin product WO 00/3736.

23. Substituted tetrahydrofuran analogs of prostaglandins as ocular hypotensives WO 97/23223.

24. $EP_2$-receptor agonists as agents for lowering intraocular pressure WO 95/19964.

25. Prostaglandin derivatives devoid of side-effects for the treatment of glaucoma. WO 99/02165.

26. 8-Iso prostaglandins for glaucoma therapy WO 98/50024; U.S. Pat. No. 6,037,368 Mar. 14, 2000.

27. Fluorinated prostaglandin derivatives and medicines WO 98/12175.

Process for Making Amino Acid Prostaglandin Salts

It has surprisingly been discovered that the disadvantages of the difficult procedures used to solidify prostaglandin free acids can be overcome by making a basic amino acid salt of the free acid which can be easily crystallized and/or recrystallized as needed.

The general process for making the amino acid prostaglandin salts according to the present invention is depicted below in Scheme I:

Scheme I

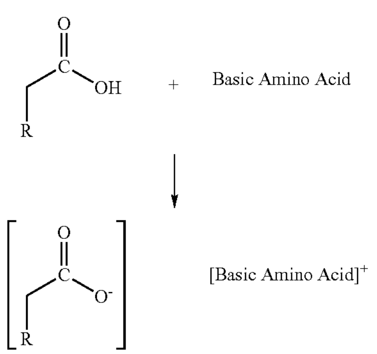

A prostaglandin free acid is reacted with an amino acid in an appropriate solvent to generate the amino acid prostaglandin salt. Solvents can vary but methanol, ethanol, water, THF are generally acceptable solvents.

The temperature of the reaction is suitably kept between −78° C. and the ambient room temperature (about 20-25° C.). Alternatively, the temperature is from about 0° C. to about 20° C. The reaction is stirred for about 5 minutes to about 4 hours under these conditions until a precipitate forms, at which point the amino acid prostaglandin salt is removed by filtration.

The salt may be recrystallized by well-known methods in the art. One suitable method is to dissolve the salt in an alcohol, such as methanol, ethanol or isopropanol, and then add diethyl ether or ethyl acetate until the cloud point, then cool to create a precipitate. The nascent precipitate is then warmed to resolubilize the material and then slowly cooled to create crystals.

Prostaglandin free acids can be made from known starting materials and methods known to one of ordinary skill in the art. For example, many are also available from Cayman Chemical Company, Ann Arbor, Mich. In addition, the following reference describes the synthesis of prostaglandins: Corey, E. J.; Weinshenker, N. M.; Schaaf, T. K.; Huber, W *J. Am. Chem. Soc.,* 1969, 91, 5675 and Corey, E. J.; Schaaf, T. K.; Huber, W; Koelliker, U.; Weinshenker, N. M.; *J. Am. Chem. Soc.,* 1970, 92, 397 (which is incorporated by reference herein).

Suitably, the prostaglandin free acid is a compound of Formula II:

II

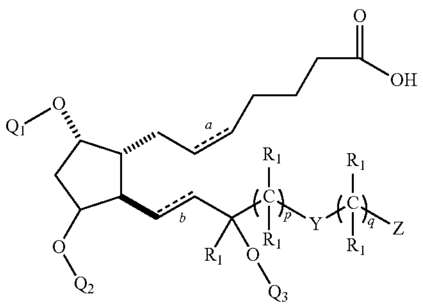

or optical isomers, diastereomers, or enantiomers thereof;

wherein a and b are, independently, single, double or triple bonds;

wherein $Q_1$, $Q_2$, and $Q_3$ are independently selected from hydrogen or an alcohol protecting group;

wherein each $R_1$ is, independently selected from hydrogen or lower alkyl;

wherein Y is —O—, —S—, —S(O), —$SO_2$—, —C$(R^2)_2$—, —$NR^1$—, —$CR^2$═$CR^2$—, or —C≡C—;

wherein Z is selected from hydrogen, carbocycle, aryl or heteroaryl;

wherein each $R^2$, if present, is independently selected from hydrogen, lower alkyl, alkoxy, or hydroxyl; and wherein p, and q are independently an integer of from 0 to 4.

Synthesis of Prostaglandins

The amino acid prostaglandin salts can be converted into prostaglandins or prostaglandin analogs in various ways. In one embodiment, the free acid is recovered by neutralizing the salt. The free acid can then be converted into a prostaglandin analog without isolation. Alternatively, the free acid can be isolated. Once the free acid is isolated, the free acid can be used itself or it can be converted to a prostaglandin analog. For example, the amino acid prostaglandin salts according to the present invention may be converted into prostaglandin analogs by neutralization of the salt, extraction of the free acid into an organic layer, leaving the amino acid behind in the aqueous layer. The organic layer can then, for example, be reacted with an additional reagent to provide a prostaglandin ester. In another embodiment, the salt can be directly converted to a prostaglandin analog without isolation of the free acid.

In other embodiments, the salt may be directly converted to a prostaglandin analog by redissolving the salt in a suitable solvent, such as methanol, and adding an additional reagent to convert the salt directly into a prostaglandin analog. Suitable reagents include primary, allylic and benzylic bromides and primary and secondary iodides such as 2-iodopropane or compounds such as bromomethane or iodomethane which make the esters of the free acids, and primary or secondary amines which, in the presence of activating agents such as EDC, produce amides.

For example, the salt of a PGF analog may be dissolved in methanol or acetone and 2 equivalents of isopropyl iodide are added. A reaction ensues to make the isopropyl ester of the PGF analog. Isopropyl esters of prostaglandins are suitable for use in the treatment of glaucoma with some PGF analogs. In another embodiment, the salt of a PGF analog may be reacted directly with N-ethyl amine to produce an amide by dissolving the salt in DMF, then adding the amine and EDC, with a small amount of DMAP, and isolating the n-ethyl amide product.

If the prostaglandin free acid is desired, it can be recovered by neutralizing the salt. For example, the salt of a PGF analog is neutralized with a 3:1 mixture of saturated aqueous ammonium chloride and 1 molar hydrochloric acid, and then the organic layer, containing the free acid, can be separated from the aqueous layer containing the amino acid.

A prostaglandin intermediate salt may similarly be either directly converted to a prostaglandin analog by either isolation or by converting the salt directly into a prostaglandin analog or further intermediate thereof as is discussed above.

Methods of Treatments Using Amino Acid Prostaglandin Salts

The amino acid prostaglandin salts may be used to treat various conditions, including eye disorders, such as glaucoma, osteoporosis, improving nasal patency or treating neurogenic bladder. The amino acid prostaglandin salts of the present invention are also useful in a method of reducing or decreasing intraocular pressure.

In one embodiment, a cell is contacted with an amount of an amino acid prostaglandin salt effective to reduce ocular pressure. The term "contacting a cell" is used to mean contacting a cell in vitro or in vivo (i.e., in a subject, such as a mammal, including humans, rabbits, cats and dogs). In some embodiments, the cell may be contacted as a result of administration of an amino acid prostaglandin salt to a subject. The term "administration" contemplates any route known to one of ordinary skill in the art, including, but not limited to, oral, topical, parenteral, injection, inhalation, implants, buccal and rectal.

An effective amount of an amino acid prostaglandin salt according to the present invention will vary with the particular condition being treated, the age and physical condition of the patient being treated, the severity of the condition, the duration of treatment, the nature of concurrent therapy, the route of administration, the particular pharmaceutically-acceptable carrier utilized, and like factors within the knowledge and expertise of the attending physician. For example, an effective amount of the amino acid prostaglandin salts of the present invention for systemic administration is from about 0.01 to about 1000 μg/kg body weight, preferably from about 0.1 to about 100 μg/kg per body weight, most preferably form about 1 to about 50 μg/kg body weight per day. Transdermal dosages would be designed to attain similar serum or plasma levels, based upon techniques known to those skilled in the art of pharmacokinetics and transdermal formulations. Plasma levels for systemic administration are expected to be in the range of 0.01 to 100 ng/mL, more preferably from 0.05 to 50 ng/mL and most preferably from 0.1 to 10 ng/mL. While these dosages are based upon a daily administration rate, the amino acid prostaglandin salts of the present invention may also be administered at other intervals, such as twice per day, twice weekly, once weekly, or once a month. One of ordinary skill in the art would be able to calculate suitable effective amounts for other intervals of administration.

Compositions Comprising Amino Acid Prostaglandin Salts

In one embodiment, the amino acid prostaglandin salts are administered in a pharmaceutically acceptable composition, such as in or with a pharmaceutically acceptable carrier.

Compositions may include one or more of the isoforms of the amino acid prostaglandin salts of the present invention. When racemates exists, each enantiomer or diastereomer may be separately used, or they may be combined in any proportion. Where tautomers exist all possible tautomers are specifically contemplated.

Pharmaceutical compositions for use in accordance with the present invention may be formulated in a conventional manner using one or more physiologically acceptable carriers or excipients. Thus, the amino acid prostaglandin salts may be formulated for administration by, for example, solid dosing, eyedrop, in a topical oil-based formulation, injection, inhalation (either through the mouth or the nose), implants, or oral, buccal, parenteral or rectal administration. Techniques and formulations may generally be found in "Remington's Pharmaceutical Sciences", (Meade Publishing Co., Easton, Pa.).

The route by which the amino acid prostaglandin salts of the present invention (component A) will be administered and the form of the composition will dictate the type of carrier (component B) to be used. The composition may be in a variety of forms, suitable, for example, for systemic administration (e.g., oral, rectal, nasal, sublingual, buccal, implants, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic or topical composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic or topical composition is typically about 5 to about 10%.

Ingredient c) is a binder. Suitable binders for solid dosage forms include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%, and in ocular solid dosing forms up to 99%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic or topical composition is typically about 0.1 to about 10%.

Ingredient e) for solid dosage forms is a colorant such as an FD&C dye. When used, the amount of ingredient e) in the systemic or topical composition is typically about 0.005 to about 0.1%.

Ingredient f) for solid dosage forms is a flavor such as menthol, peppermint, and fruit flavors. The amount of ingredient f), when used, in the systemic or topical composition is typically about 0.1 to about 1.0%.

Ingredient g) for solid dosage forms is a sweetener such as aspartame and saccharin. The amount of ingredient g) in the systemic or topical composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic or topical composition is typically about 0.1 to about 5%.

Ingredient j) is a preservative such as benzalkonium chloride, methyl paraben and sodium benzoate. The amount of ingredient j) in the systemic or topical composition is typically about 0.01 to about 5%.

Ingredient k) for solid dosage forms is a glidant such as silicon dioxide. The amount of ingredient k) in the systemic or topical composition is typically about 1 to about 5%.

Ingredient m) is a solvent, such as water, isotonic saline, ethyl oleate, glycerine, hydroxylated castor oils, alcohols such as ethanol, and phosphate buffer solutions. The amount of ingredient m) in the systemic or topical composition is typically from about 0 to about 100%.

Ingredient n) is a suspending agent. Suitable suspending agents include Avicel® RC-591 (from FMC Corporation of Philadelphia, Pa.) and sodium alginate. The amount of ingredient n) in the systemic or topical composition is typically about 1 to about 8%.

Ingredient o) is a surfactant such as lecithin, Polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic or topical composition is typically about 0.1% to about 5%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the amino acid prostaglandin salts of the present invention and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including implants, time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics. Implants can be of the biodegradable or the non-biodegradable type. Implants may be prepared using any known biocompatible formulation.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject amino acid prostaglandin salts include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the amino acid prostaglandin salts of the present invention are topically administered. Topical compositions that can be applied locally to the eye may be in any form known in the art, non-limiting Examples of which include solids, gelable drops, sprays, ointments, or a sustained or non-sustained release unit placed in the conjunctival cul-du-sac of the eye or another appropriate location.

Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions comprise: component A, the amino acid prostaglandin salts described above, and component B, a carrier. The carrier of the topical composition preferably aids penetration of the amino acid prostaglandin salts into the eye. Component B may further comprise one or more optional components.

The exact amounts of each component in the topical composition depend on various factors. The amount of component A added to the topical composition is dependent on the IC50 of component A, typically expressed in nanomolar (nM) units. For example, if the IC50 of the medicament is 1 nM, the amount of component A will be from about 0.001 to about 0.3%. If the IC50 of the medicament is 10 nM, the amount of component A) will be from about 0.01 to about 1%. If the IC50 of the medicament is 100 nM, the amount of component A will be from about 0.1 to about 10%. If the IC50 of the medicament is 1000 nM, the amount of component A will be 1 to 100%, preferably 5% to 50%. If the amount of component A is outside the ranges specified above (i.e., lower), efficacy of the treatment may be reduced. One skilled in the art understands how to calculate and understand an IC50. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include water, ethyl alcohol and propylene glycol.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical composition is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not typically used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is generally not used.

In a particularly preferred embodiment of the invention, topical pharmaceutical compositions for ocular administration are prepared typically comprising component A and B (a carrier), such as purified water, and one or more ingredients selected from the group consisting of y) sugars or sugar alcohols such as dextrans, particularly mannitol and dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 5.0-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

EXAMPLES

The following non-limiting examples further illustrate the processes of the present invention:

Example 1

Preparation of Latanoprost Arginine Salt (E1):

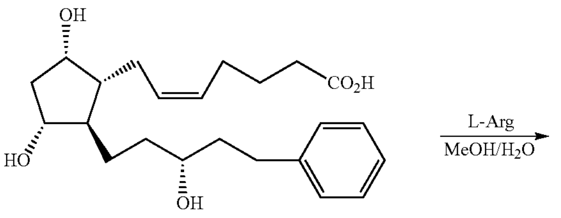

1

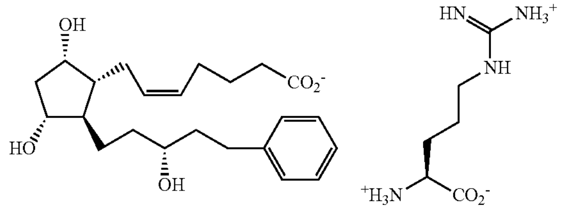

2

To Latanoprost free acid (CAS # 41639-83-2) (1, 21.2 mg, 0.054 mmol) in $MeOH/H_2O$ (4:1, 0.65 mL) was added L-Arginine (>98%, Sigma-Aldrich, St. Louis, Mo.). (72 mM solution in $MeOH/H_2O$ [4:1]) (754 μL, 0.054 mmol) and the solution was stirred for 30 minutes. The solvents were evaporated then azeotroped with $Et_2O$ and hexanes to give white crystalline Latanoprost-L-Arginine salt 2 (quantitative).

Recrystallization: To 26.5 mg of 1 in a 4 mL vial was added approx 0.5 mL of MeOH to dissolve, followed by 1.2-1.5 mL of $Et_2O$ which precipitated out the product. The vial was put on ice for 5 min. The liquid was decanted and the solid dried to give pure 2, 22.9 mg.

Example 2

Using substantially the same procedure, but substituting $PGE_2$ free acid (CAS #: 363-24-6) for latanoprost free acid the arginine salt of $PGE_2$ can be made.

Examples 3-71

Arginine salts of the following commercially-available prostaglandins can be made by following the above procedure and substituting the appropriate prostaglandin free acid

| Example | Free acid name | CAS # |
|---|---|---|
| 3 | 8-iso Prostaglandin F2α | 27415-26-5 |
| 4 | Prostaglandin D2 | 41598-07-6 |
| 5 | Prostaglandin E1 | 745-65-3 |
| 6 | Prostaglandin F2α | 551-11-1 |
| 7 | Prostaglandin D3 | 71902-47-1 |
| 8 | 16,16-dimethyl Prostaglandin E2 | 39746-25-3 |
| 9 | Butaprost (free acid) | 433219-55-7 |
| 10 | Tafluprost (free acid) | 209860-88-8 |
| 11 | Bimatoprost (free acid) | |
| 12 | Prostaglandin A1 | 14152-28-4 |
| 13 | Travoprost (free acid) | |
| 14 | Latanoprost (free acid)-d4 | |
| 15 | 17-phenyl trinor Prostaglandin E2 | 38315-43-4 |
| 16 | 15(S)-Latanoprost (free acid) | |
| 17 | AL 8810 | 246246-19-5 |
| 18 | Bimatoprost (free acid) | 38344-08-0 |
| 19 | (+)-15-epi Cloprostenol | 54276-22-1 |
| 20 | 15-keto Latanoprost (free acid) | |
| 21 | Prostaglandin E3 | 802-31-3 |
| 22 | Limaprost | 74397-12-9 |
| 23 | (+)-Fluprostenol (also know as travoprost free acid) | 54276-17-4 |
| 24 | BW 245C | 72814-32-5 |
| 25 | Δ12-Prostaglandin J2 | 87893-54-7 |
| 26 | 11β-Prostaglandin F2α | 38432-87-0 |
| 27 | 5-trans Prostaglandin E2 | 36150-00-2 |
| 28 | 19(R)-hydroxy Prostaglandin E2 | 64625-54-3 |
| 29 | Fluprostenol (racemic) | 40666-16-8 |
| 30 | Prostaglandin F2β | 4510-16-1 |
| 31 | 16-phenoxy tetranor Prostaglandin E2 | |
| 32 | (+)-Cloprostenol | 54276-21-0 |
| 33 | 20-hydroxy Prostaglandin E2 | 57930-95-7 |
| 34 | 17,20-dimethyl Prostaglandin F1α | |
| 35 | (+)-Cloprostenol | |
| 36 | 9-keto Fluprostenol | 156406-33-6 |
| 37 | Prostaglandin F1α | 745-62-0 |
| 38 | 15(S)-Fluprostenol | |
| 39 | 5-trans Prostaglandin F2β | 36150-02-4 |
| 40 | 15-keto-17-phenyl trinor Prostaglandin F2α | |
| 41 | 15-cyclohexyl pentanor Prostaglandin F2α | 58611-97-5 |
| 42 | Cloprostenol (racemic) | |
| 43 | Prostaglandin F1β | 10164-73-5 |
| 44 | 3-methoxy Limaprost | |
| 45 | 13,14-dihydro Prostaglandin F2α | 27376-74-5 |
| 46 | 15(R)-15-methyl Prostaglandin E2 | 55028-70-1 |
| 47 | 19(R)-hydroxy Prostaglandin E1 | 64625-55-4 |
| 48 | 9-deoxy-9-methylene Prostaglandin E2 | 61263-32-9 |
| 49 | 16-phenyl tetranor Prostaglandin E1 | |
| 50 | 11-deoxy Prostaglandin F1α | 37785-98-1 |
| 51 | 19(R)-hydroxy Prostaglandin F1α | 81371-59-7 |
| 52 | 19(R)-hydroxy Prostaglandin F2α | 64625-53-2 |
| 53 | 1a,1b-dihomo Prostaglandin F2α | 57944-39-5 |
| 54 | 15(R),19(R)-hydroxy Prostaglandin F2α | |
| 55 | 16-phenoxy tetranor Prostaglandin F2α | 51705-19-2 |
| 56 | 11-deoxy Prostaglandin F1β | 37785-99-2 |
| 57 | 11-deoxy Prostaglandin F2β | 37786-07-5 |
| 58 | 11β-Prostaglandin F1β | 37785-86-7 |
| 59 | 15-keto Fluprostenol | |
| 60 | 15(S)-15-methyl Prostaglandin F2α | 35700-23-3 |
| 61 | 16,16-dimethyl Prostaglandin E1 | 41692-15-3 |
| 62 | 16,16-dimethyl Prostaglandin F2α | 39746-23-1 |
| 63 | 17-trifluoromethylphenyl-13,14-dihydro trinor Prostaglandin | |
| 64 | 17-trifluoromethylphenyl trinor Prostaglandin F2α | 221246-34-0 |
| 65 | Bimatoprost (free acid)-d4 | |
| 66 | (+)-Fluprostenol-d4 | |
| 67 | Prostaglandin B2 | 13367-85-6 |
| 68 | Prostaglandin B3 | 36614-32-1 |
| 69 | 17-phenyl trinor Prostaglandin A2 | |
| 70 | (S)-AL 8810 | |
| 71 | Lubiprostone | 136790-76-6 |

Example 72

To Latanoprost (free acid) (1, 21.2 mg, 0.054 mmol) in $MeOH/H_2O$ (4:1, 0.65 mL) was added L-Arginine (72 mM solution in MeOH/$H_2O$ [4:1]) (754 μL, 0.054 mmol) ((>98%) from Sigma-Aldrich Cat. A5006) and the solution was stirred for 30 minutes. The solvents were evaporated then azeotroped with $Et_2O$ and hexanes to give white crystalline Latanoprost-L-Arginine salt 2 (quantitative).

Recrystallization: To 26.5 mg of 1 in a 4 mL vial was added approx 0.5 mL of MeOH to dissolve, followed by 1.2-1.5 mL of $Et_2O$ which precipitated out the product. The vial was put on ice for 5 min. The liquid was decanted and the solid dried to give pure 2, 22.9 mg.

Example 73

To travoprost free acid ((+)-fluprostenol free acid) 3 in MeOH/$H_2O$ was added L-Arginine (>98%) (Sigma-Aldrich Cat. A5006) and the solution was stirred for 30 minutes. The solvents were evaporated then azeotroped with $Et_2O$ and hexanes to give white crystalline travoprost-L-Arginine salt 4 (quantitative).

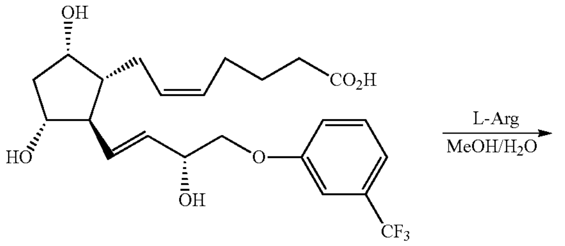

3

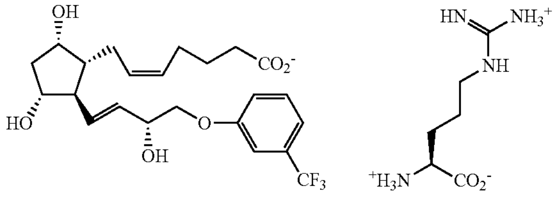

4

Recrystallization: To 4 is added enough MeOH to dissolve, and is followed by $Et_2O$ to the cloud point, then warmed to redissolved and slowly cooled overnight. The liquid is decanted and the solid is dried to give pure 4.

Example 74

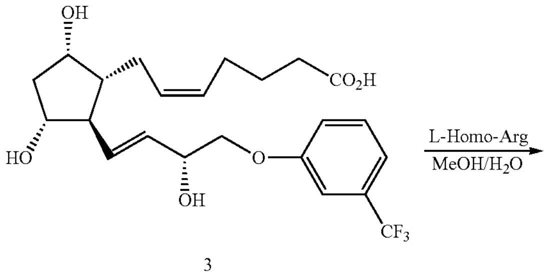

3

-continued

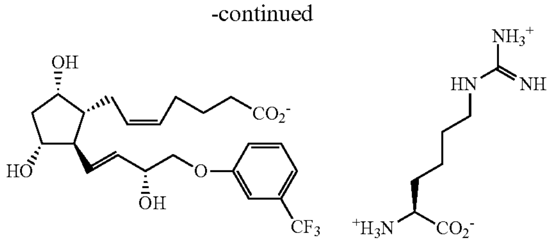

5

To travoprost free acid ((+)-fluprostenol free acid) 3 in MeOH/$H_2O$ is added L-Homoarginine and the solution is stirred for 30 minutes. The solvents are evaporated then azeotroped with $Et_2O$ and hexanes to give white crystalline travoprost-L-Homoarginine salt 5 (quantitative).

Recrystallization: To 5 was added enough EtOH to dissolve, followed by $Et_2O$ which precipitated the product. The vial was put on ice for 5 min. The liquid was decanted and the solid dried to give the salt 5.

Example 75

Formulation of Liquid Compositions Comprising Present Compounds

A composition in liquid form is prepared by conventional methods, formulated as follows:

EXAMPLE 75

Preparation Table

| Ingredient | Quantity |
|---|---|
| PGF analog arginine salt | 0-5 mg |
| PGE analog arginine salt | 0-5 mg |
| Propylene glycol | 5 mL |
| Ethyl alcohol | 5 mL |

1.0 mL of the above composition, when administered once a day, substantially increases the beauty and health of the mammalian skin onto which it is applied.

Example 76

Preparation of Skin Care Topical Product Comprising Present Compounds

A skin care, topical product is prepared by formulating a cream composition as illustrated below.

EXAMPLE 76

Preparation Table

| Ingredient | Quantity |
|---|---|
| PGF analog arginine salt | 50 mg |
| Isopropyl isosterate | 150 g |
| Polyacrylate 13/polyisobutene/Polysorbate 20 | 35 g |
| Methyl paraben/propyl paraben | 1 g |
| Distilled water | 400 g |

Example 77

Preparation of Skin Care Wipe Product Comprising Present Compounds

A skin care wipe product is prepared by impregnating such a wipe with the liquid composition of Example 75. Such a wipe may be impregnated by techniques known and readily available to those skilled in the art. Indeed, a preferred example of a wipe product is the Oil of Olay Facial Wipes, owned and distributed by The Procter and Gamble Company of Cincinnati, Ohio.

Example 78

Shampoos are made, comprising:

| Component | Ex. 78-1 | Ex. 78-2 | Ex. 78-3 | Ex. 78-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| PGF analog arginine salt | — | 0.2% | 0.2% | — |
| PGE analog arginine salt | 0.1% | — | — | 0.1% |
| Minoxidil | | | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

A human subject suffering from male pattern baldness is treated by a method of this invention. Specifically, for 12 weeks, a shampoo described above is used daily by the subject. Approximately one liquid ounce of the formula is applied to the scalp and hair of the subject, left in place for not more than 5 minutes, then rinsed with water.

Example 79

Topical pharmaceutical compositions for lowering intraocular pressure are prepared by conventional methods and formulated as follows:

| Ingredient | Amount (wt %) |
|---|---|
| PGF analog arginine salt | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 7.0-7.2 |
| Purified water | q.s. to 100% |

A compound according to this invention is used as the PF analog arginine salt. When the composition is topically administered to the eyes as a 40 microliter drop instilled into the affected eye once daily, the above composition decreases intraocular pressure in a patient suffering from glaucoma.

Example 80

Example 79 is repeated using a PGE analog arginine salt according to this invention. When administered as a drop twice per day, the above composition substantially decreases intraocular pressure.

Example 81

Topical pharmaceutical compositions for nasal sprays are prepared by conventional methods and formulated as follows:

| Ingredient | Amount (wt %) |
|---|---|
| PGF analog arginine salt | 0.1-0.50 |
| Hydroxypropyl methylcellulose | 0.0-0.3 |
| Sorbitol | 0.61 |
| EDTA | 0.05 |
| Benzalkonium chloride | 0.01 |
| HCl and/or NaOH to | pH 7.0-7.2 |
| Purified water | q.s. to 100% |

Example 82

Topical pharmaceutical compositions for instillation, e.g., into a bladder are prepared by conventional methods and formulated as follows:

| Ingredient | Amount (wt %) |
|---|---|
| PGF analog arginine salt | 0.1-0.50 |
| EDTA | 0.05 |
| Phosphate buffered saline | q.s. to 100% |

Example 83

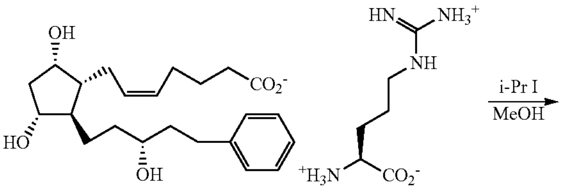

2

-continued

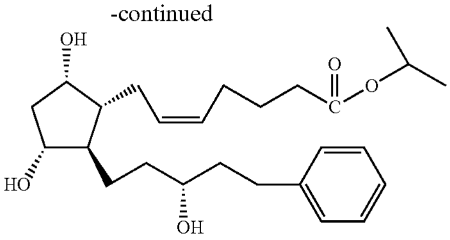

6

To 1.0 gram of Latanoprost L-arginine salt (2) in MeOH/$H_2O$ (4:1, 20 mL) is added 2.01 equivalents of isopropyl iodide (99%, Cat #148938, Sigma-Aldrich, St. Louis, Mo.). and the solution is stirred overnight. Saturated aqueous ammonium acetate is added along with ethyl acetate and the layers are separated. The organic layer is separated, and the solvents removed in vaccuo, and the material is chromatographed to give latanoprost as the isopropyl ester (6).

Example 84

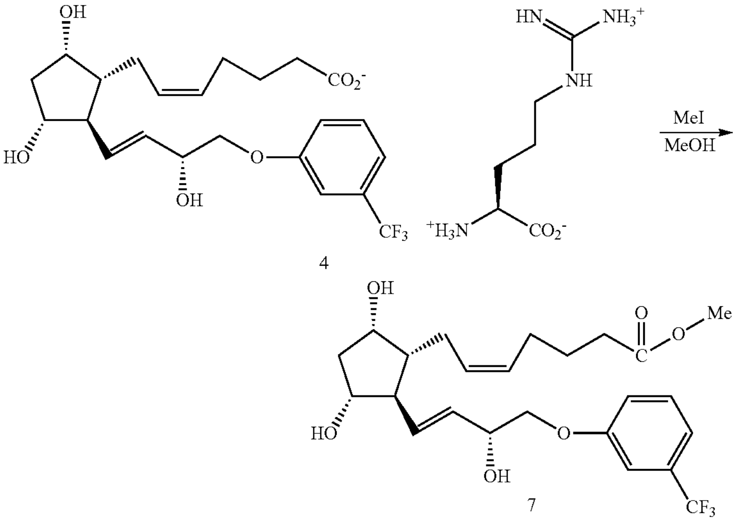

4

7

The procedure of example 83 is repeated substituting fluprostenol for latanoprost and methyl iodide for isopropyl iodide. Isolated is fluprostenol methyl ester (7)

Example 85

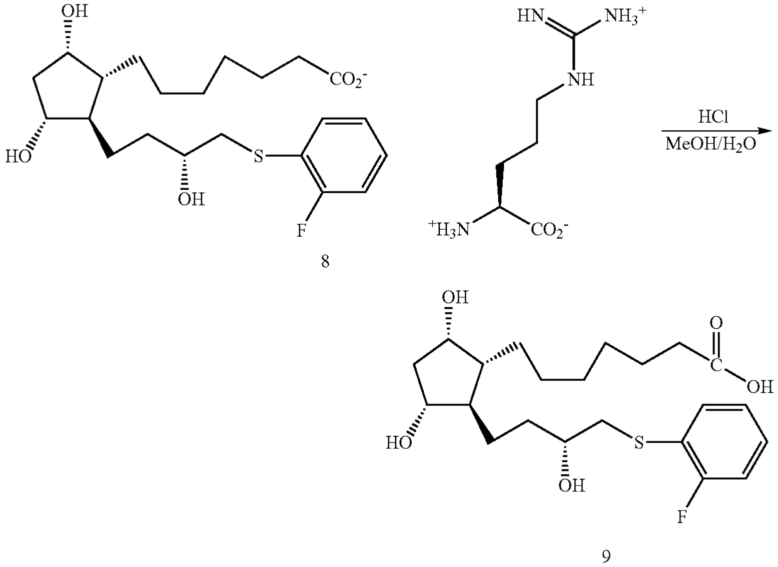

8

9

To 1.0 gram of Arginyl 7-((1R,2R,3R,5S)-2-((R)-4-(2-fluorophenylthio)-3-hydroxybutyl)-3,5-dihydroxy cyclopentyl)heptanoate (8) in MeOH/$H_2O$ (4:1, 20 mL) is added, dropwise with cooling, at least 5 equivalents of a 3:1 mixture of saturated aqueous ammonium chloride and 1 M hydrochloric acid (Sigma-Aldrich, St. Louis, Mo.), and the solution is stirred for 15 minutes. Saturated aqueous sodium chloride is added along with ethyl acetate. The organic layer is separated; is washed again with brine; the solvents removed in vaccuo, and the material chromatographed to give the free acid, 7-((1R,2R,3R,5S)-2-((R)-4-(2-fluorophenylthio)-3-hydroxybutyl)-3,5-dihydroxy cyclopentyl)heptanoic acid (9).

Example 86

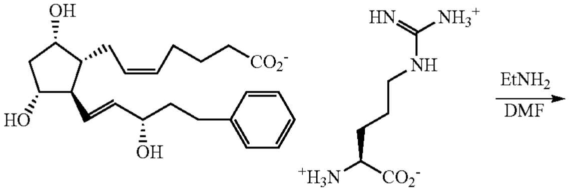

9

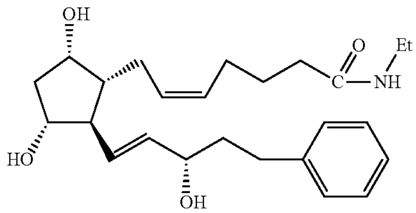

10

To 1.0 gram of bimataprost arginine salt (9) in DMF (20 mL) is added 2.01 equivalents of 2M ethyl amine solution in THF (Cat #395072, Sigma-Aldrich, St. Louis, Mo.) and 1.5 eq of EDC. and the solution is stirred overnight. Added is at least 5 equivalents of a 3:1 mixture of saturated aqueous ammonium chloride and 1 M hydrochloric acid (Sigma-Aldrich, St. Louis, Mo.), and the solution is extracted with ethyl acetate, washed and purified. Isolated is bimataprost N-ethyl amide (10)

Example 87

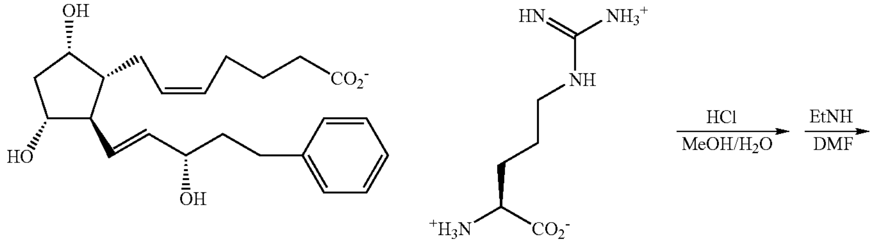

9

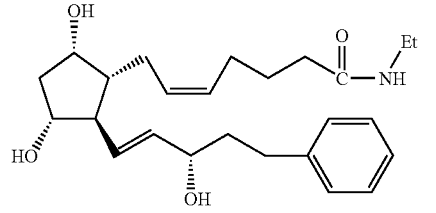

10

To 1.0 gram of bimataprost arginine salt (9) is added at least 5 equivalents of a 3:1 mixture of saturated aqueous ammonium chloride and 1 M hydrochloric acid (Sigma-Aldrich, St. Louis, Mo.), and the solution is extracted with diethyl ether. The organic layer is then separated, and added are: 20 mL of DMF, 2.01 equivalents of 2M ethyl amine solution in THF (Cat #395072, Sigma-Aldrich, St. Louis, Mo.), 1.5 eq of EDC and 0.2 eq. of DMAP, and the solution is stirred overnight. Then added is at least 5 equivalents of a 3:1 mixture of saturated aqueous ammonium chloride and 1 M hydrochloric acid (Sigma-Aldrich, St. Louis, Mo.), and the solution is extracted with ethyl acetate, washed and purified. Isolated is bimataprost N-ethyl amide (10)

The invention claimed is:

1. Latanoprost free acid arginine salt, wherein the free acid salt is crystalline.

2. The salt according to claim 1, wherein the salt is a product of a reaction between latanoprost free acid and arginine.

3. A pharmaceutical composition comprising a salt according to claim 1 and a pharmaceutically acceptable carrier.

4. A method of treating glaucoma disease comprising administering to a subject in need thereof an effective amount of a salt according to claim 1.

5. A method of improving nasal patency or treating neurogenic bladder comprising administering to a subject in need thereof an effective amount of a salt according to claim 1.

6. A method of treating osteoporosis comprising administering to a subject in need thereof an effective amount of a salt according to claim 1.

7. A method of reducing ocular pressure comprising contacting a cell with an amount of a salt according to claim 1 effective to reduce ocular pressure.

8. The method of claim 7, wherein the cell is in a subject.

* * * * *